(12) United States Patent
Yang et al.

(10) Patent No.: US 7,160,986 B2
(45) Date of Patent: Jan. 9, 2007

(54) BCL-Xγ, A NOVEL BCL-X ISOFORM, AND USES RELATED THERETO

(75) Inventors: Xiao-Feng Yang, Brookline, MA (US); Georg F. Weber, Chestnut Hill, MA (US); Harvey Cantor, Belmont, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 364 days.

(21) Appl. No.: 10/208,155

(22) Filed: Jul. 29, 2002

(65) Prior Publication Data

US 2003/0013171 A1 Jan. 16, 2003

Related U.S. Application Data

(62) Division of application No. 08/899,367, filed on Jul. 23, 1997, now Pat. No. 6,472,170.

(60) Provisional application No. 60/023,666, filed on Aug. 2, 1996.

(51) Int. Cl.
*C07K 14/47* (2006.01)
(52) U.S. Cl. .................. 530/350; 435/69.1; 435/69.7
(58) Field of Classification Search ................ 530/350; 435/69.1, 69.9
See application file for complete search history.

(56) References Cited

U.S. PATENT DOCUMENTS 5,789,201 A * 8/1998 Guastella .................... 435/69.1

FOREIGN PATENT DOCUMENTS

| WO | WO 95/00642 | 1/1995 |
|----|-------------|--------|
| WO | WO 95/10630 A1 | 4/1995 |
| WO | WO 96/40941 A1 | 12/1996 |

OTHER PUBLICATIONS

The Merck Index, Ninth edition (Windholz et al., eds) Rahway NJ, 1976. p. 582.*
Yang et al. Analysis of the complex genomic structure of Bcl -x and its relationship☐☐to Bcl -x(gamma) expression after CD28-dependent costimulation. 2002 Molecular immunology 39 (1-2) p. 45-55.*
Boise, Lawrence, et al. bcl-x, A bcl-2-Related Gene That Functions as a Dominant Regulator of Apoptotic Cell Death, *Cell Press*, vol. 74, pp. 597-608, Aug. 27, 1993.
Callard et al. *The Cytokine FactsBook*, New York, Academic Press. p. 31, 1994.
Chan et al. Identification of human and mouse p19, a novel CDK14 and CDK8 inhibitor with homology to p16ink4. *Mol. Cell Biol.* 15(5): 2682-2688, May 1995.
Ma, Averil, et al. "Bclx Regulates The Survival of Double-Positive Thymocytes", *Proc. Natl. Acad. Sci. USA*, vol. 92, pp. 4763-3767, May 1995.

Fang W. et al. Cloning and molecular characterization of mouse bcl-x in B and T lymphocytes. *J. Immunol.* Nov. 15, 1994;153(10):4388-98.
Farrow, Stuart, et al., "New Members of the Bcl-2 Family and Their Protein Partners", *Current Opinion in Genetics & Development*, vol. 6, pp. 45-49, 1996.
Gorina, Svetlana, et al. "Structure of the p53 Tumor Suppressor Bound to the Ankyrin and SH3 Domains of 53BP2", *Science*, vol. 274, pp. 1001-1005, Nov. 8, 1996.
Grillot, Didier, et al. "Bcl-$x_L$ Displays Restricted Distribution During T Cell Development and Inhibits Multiple Forms of Apoptosis But Not Clonal Deletion in Transgenic Mice", *J. Exp. Med.*, vol. 182, pp. 1973-1983, Dec. 1995.
Grillot, Didier, et al. Genomic organization, promoter region anlaysis, and chromosome localization of the mouse bcl-x gene. *J Immunol.* May 15, 1997;158(10):4750-7.
Ohno, Hitoshi, et al., "The Candidate Proto-Oncogene bcl-3 Is Related To Genes Implicated IN Cell Lineage Determination and Cell Cycle Control", *Cell*, vol. 60, pp. 991-997, Mar. 23, 1990.
Yang et al, "Cloning of BCL-Xγ, A New BCL-X Isoform That is Preferentially Expressed In $CD4^+$ T Cells", *The FASEB Journal Abstracts*, Apr. 30, 1996, vol. 10, No. 6, A412.
Hatada, Eunice, et al., "The Ankyrin Repeat Domains of the NF-kB Precursor p105 and the Protooncogene bcl-3 Act As Specific Inhibitors of NF-kB DNA Binding", *Proc. Natl. Acad. Sci. USA*, vol. 89, pp. 2489-2493, Mar. 1992.
Genbank Accession No. L35049 Gonzalez-Garcia et al. Mus musculus Bcl-xL mRNA, complete cds. Nov. 5, 1994, Bethesda National Library of Medicine.
Genbank Accession No. S76513, Tilly et al. bcl-x=apoptosis inhibitor (protooncogene) [rats, ovary, mRNA Partial, 726 nt].Sep. 26, 1995 Bethesda: National Library of Medicine.
Genbank Accession No. X82537 Michaelidis et al. R.norvegicus bcl-x gene. Dec. 31, 1994. Bethesda: National Library of Medicine.
Genbank Accession No. D30746, Inhohara et al. Homo sapiens gene for Bcl-x protein, promoter region and exon 1 and 2. Jun. 24, 1995 Bethesda: National Library of Medicine.
Genbank Accession No. Z23115 Boise et al H.sapiens bcl-xL mRNA. Jul. 26, 1994. Bethesda: National Library of Medicine.
Genbank Accession No. X83574, M. musculus bcl-xL mRNA, Jul. 26, 1994 Bethesda: National Library of Medicine.
Genbank Accession No. U10101, Fang et al Mus musculus bcl-x long (bcl-x long) mRNA, complete cds.. Nov. 30, 1995 Bethesda: Nat'l Library of Medicine.

(Continued)

*Primary Examiner*—Gabriele Bugaisky
(74) *Attorney, Agent, or Firm*—Foley Hoag, LLP

(57) ABSTRACT

The present invention relates to BCL-xγ, a novel isoform of the BCL-x family of proteins which is predominantly expressed in T-lymphocytes and is associated with resistance to apoptosis. Both compositions of matter and methods are described which are useful in the treatment or prevention of immune system disorders.

5 Claims, 14 Drawing Sheets

OTHER PUBLICATIONS

Genbank Accession No. U10102, Fang et al. Mus musculus bcl-x transmembrane deleted (bcl-x long) mRNA, complete cds. Nov. 30, 1995 Bethesda: National Library of Medicine.

Genbank Accession No. U10579, Wesselingh et al. Rattus norvegicus Bcl-x (bcl-x) gene, complete cds. Jun. 28, 1994 Bethesda: National Library of Medicine.

Tilly, J.L. et al. Expression of members of the bcl-2 gene family in the immature rat ovary: equine chorionic gonadotropin-mediated inhibition of granulosa cell apoptosis is associated with decreased bax and constitutive bcl-2 and bcl-xlong messenger ribonucleic acid levels. *Endocrinology*. Jan. 1995;136(1):232-41.

* cited by examiner

FIGURE 1A

```
           10                  30                  50
cattcctcctgagataaggccctcgatctggtcgatggaggaaccaggttgtgaggggc
           70                  90                 110
aggttcctaagcttcgcaattcctctgtcgccttctgagctgcctaccaggtcgcatgat
          130                 150                 170
cctccggccggggctggtttttttttttttttttttttgctgagttaccggcgacc
          190                 210                 230
cagccaccacctcctccccgacctatgatacaaaagaccttccggggggttgtacctgctt
          250                 270                 290
gctgtcgccggagatagatttgaataaccttatcttggctttggatcctggaagagaatc
          310                 330                 350
gctaaacacagagcagacccagtaagtgagcaggtgttttggacaatggactggttgagc
          370                 390                 410
ccatctctattataaaaatgtctcagagcaaccgggagctggtggtcgactttctctcct
                  M  S  Q  S  N  R  E  L  V  V  D  F  L  S  Y    15
          430                 450                 470
acaagctttcccagaaaggatacagctggagtcagtttagtgatgttgaagagaatagga
         K  L  S  Q  K  G  Y  S  W  S  Q  F  S  D  V  E  E  N  R  T    35
          490                 510                 530
ctgaggccccagaagaaactgaagcagagagggagaccccagtgccatcaatggcaacc
         E  A  P  E  E  T  E  A  E  R  E  T  P  S  A  I  N  G  N  P    55
          550                 570                 590
catcctggcacctggcggatagcccggccgtgaatggagccactggccacagcagcagtt
         S  W  H  L  A  D  S  P  A  V  N  G  A  T  G  H  S  S  S  L    75
          610                 630                 650
tggatgcgcgggaggtgattcccatggcagcagtgaagcaagcgctgagagaggcaggcg
         D  A  R  E  V  I  P  M  A  A  V  K  Q  A  L  R  E  A  G  D    95
          670                 690                 710
atgagtttgaactgcggtaccggagagcgttcagtgatctaacatcccagcttcacataa
         E  F  E  L  R  Y  R  R  A  F  S  D  L  T  S  Q  L  H  I  T   115
          730                 750                 770
ccccagggaccgcgtatcagagctttgagcaggtagtgaatgaactctttcgggatggag
         P  G  T  A  Y  Q  S  F  E  Q  V  V  N  E  L  F  R  D  G  V   135
          790                 810                 830
taaactggggtcgcatcgtggccttttttctcctttggcggggcactgtgcgtggaaagcg
         N  W  G  R  I  V  A  F  S  F  G  G  A  L  C  V  E  S  V   155
          850                 870                 890
tagacaaggagatgcaggtattggtgagtcggattgcaagttggatggccacctatctga
         D  K  E  M  Q  V  L  V  S  R  I  A  S  W  M  A  T  Y  L  N   175
          910                 930                 950
atgaccacctagagccttggatccaggagaacggcggctggggtgtgagtggaggtacac
         D  H  L  E  P  W  I  Q  E  N  G  G  W  G  V  S  G  G  T  P   195
          970                 990                1010
ccctcagatctgtcttcagaaggcttgttcaagtgccaggagtggcggagcacgtttgtg
         L  R  S  V  F  R  R  L  V  Q  V  P  G  V  A  E  H  V  C  D   215
         1030                1050                1070
atcccagcctttgggaggtggaaacagaaggatcggaagttcaaggccctcctcagctat
         P  S  L  W  E  V  E  T  E  G  S  E  V  Q  G  P  P  Q  L  L   235
         1090                1110                1130
tataggtttctctgtgtagccctggctgtcctgtaactcactctgtagagcaaactggac
            *
         1150                1170                1190
tcaaactcagagacatgcctgcctgatcttcatcgtgagtgctggaatcacaggctctaa
         1210                1230                1250
catggctatcgggagatgcgtggaccaggcctatggtggcccttgacgcagcgtggtgct
         1270                1290                1310
tcaactcagaccaagagacagagcagaaaatcaacagaggggacaaaaagtgtctgtgtg
         1330                1350                1370
ccaaggaccttatctcaggaggacttcaggaaggacgctgacccttccttccctcattcc
ttcg
```

FIGURE 1D

Alignment of the specific region of mouse Bcl-xγ with the consensus sequence of the ankyrin like domain

```
                    Splice site 2
                         │
                         ▼   ──▶ Bcl-xγ-specific region
Bcl-xγ              NGGWGVSGGTPLRSVFRRLVQVPGVAEHVCDPSLWEVETEGSEVQGPPQLL
Ankyrin consensus   N -----G-TPLH-A---------V--LL--GA
```

Identical amino acid residues: bold + underlined
Highly conserved amino acid residues: bold
Similar amino acid residues: underlined

A.

B.

*Expression of bcl-xγ in the thymuses of normal, cortisone-treated and mutant mice detected by RT-PCR*

Expression of bcl-xr in Balb/c thymocytes verse DBA/2 thymocytes detected by RT-PCR Expression of bcl-xr in CD69+ thymocytes verse CD69- thymocytes detected by RT-PCR Expression of bcl-xr in B6 normal mouse thymocyte, CD4+CD8+DP and SP, CD4-CD8-DN fractions, Rag-2 knock-out and TCR-β knock-out thymus detected by RT-PCR

BCL-Xγ, A NOVEL BCL-X ISOFORM, AND USES RELATED THERETO

RELATED APPLICATIONS

This application is a divisional of application Ser. No. 08/899,367 filed on Jul. 23, 1997 now U.S. Pat. No. 6,472,170 which claims the benefit of Provisional Application No. 60/023,666 filed Aug. 2, 1996. The contents of all of the aforementioned application(s) are hereby incorporated by reference.

GOVERNMENT FUNDING

Work described herein was funded, in part, by one or more grants awarded by the National Institutes of Health. The U.S. Government, therefore, may have certain rights in this invention.

BACKGROUND OF THE INVENTION

Members of the family of BCL-2-related proteins serve as regulators of programmed cell death, or apoptosis (Cory, 1995 *Annu. Rev. Immunol.* 13, 513–543; Hockenbery, 1995 *Nature* 348, 334–336; Nunez et al., 1994 *Nature* 348, 334–336; Reed, 1994. *J. Cell Biol.* 124, 1–6; Akbar et al., 1993. *Immunology Today* 14, 526–532). Apoptosis has been shown to be involved in several immune processes, including intrathymic deletion of autoreactive cells, elimination of peripheral T cells during the response to viral and bacterial superantigens and lysis of target cells by cytotoxic T lymphocytes. There is increasing evidence that clonal expansion of antigen-specific T-cells is determined by the relative level of cellular proliferation and apoptosis following TCR ligation (Zinkemagel et al. 1993. *Immunol. Rev.* 131:199). However, the genetic mechanisms responsible for regulating these response phenotypes are not well understood.

The first gene to be identified which encoded a protein in this family, bcl-2, was cloned from the chromosomal breakpoint of t(14;18)-bearing B-cell lymphomas (Tsujimoto et al., 1984. *Science* 226:1097) and shown to inhibit cellular susceptibility to apoptosis (Cory, supra).

Several genes with homology to bcl-2 have subsequently been characterized, including the following: A1, which encodes an 80-amino acid protein that is rapidly induced in macrophages in response to GM-CSF or LPS (Lin et al., 1993. *J. Immunol.* 151, 1979–1988); MCL1, an early response gene in myeloid cell lines which undergo macrophage differentiation (Kozopas et al., 1993. *Proc. Natl. Acad. Sci. USA* 90, 3516–3520); and Bak, a BCL-2 homologue that may enhance apoptosis (Chittenden et al., 1995. *Nature* 374:733; Kiefer et al., 1995. *Nature* 374:736).

The bcl-x gene product, closely related to the BCL-2-related protein family, also protects cells from apoptosis. Analysis of mice deficient in BCL-x has suggested that its function is to support the viability of immature cells during development of the nervous and hematopoietic systems (Motoyama et al., 1995. *Science* 267, 1506–1510; Ma et al., 1995. *Proc. Natl. Acad. Sci. USA* 92, 4763–4767). Alternative splicing of human bcl-x may result in at least two distinct BCL-x mRNA species. The predominant protein product (233 amino acids) of the larger BCL-x mRNA, BCL-xL, inhibits cell death upon growth factor withdrawal (Boise et al., 1993. *Cell* 74, 597–608) and its transgenic expression alters thymocyte maturation leading to increased numbers of mature thymocytes (Chao et al., 1995. *J. Exp. Med.* 182, 821–828; Grillot et al., 1995. *J. Exp. Med.* 182, 1973–1983). After coligation of CD3 and CD28 in murine T-cells, enhanced BCL-xL expression may confer protection from apoptosis (Boise et al., 1995. *Immunity* 3, 87–98; Radvanyi et al., 1996. *J. Immunol.* 156, 1788–1798; Mueller et al., 1996. *J. Immunol.* 156, 1764–1771). The contribution of other isoforms of this gene to activation-induced death in T-cells is less well-defined (Gonzalez-Garcia et al., 1994. *Development* 120, 3033–3042; Fang et al., 1994 *J. Immunol.* 153, 4388–4398). A second human BCL-x isoform, BCL-xS, encodes a smaller protein of 170 amino acids which may enhance apoptosis, suggesting that different members of the BCL-x family may have opposing functions. Additional murine BCL-x isoforms, termed BCL-xβ and BCL-xΔTM, have been defined. The β isoform may inhibit apoptosis in neurons (Gonzalez-Garcia et al., 1995. *Proc. Natl. Acad. Sci. U.S.A.* 92, 4304–4308) and the ΔTM isoform may inhibit apoptosis in B-cells (Fang et al., supra).

Several proteins which interact with BCL-2 proteins have also been identified including bax, Nip1, Nip2, Nip 3, bad, and bag-1. These various BCL-2 binding proteins have different effects on apoptosis. For example, bak and bax function as inducers of apoptosis, whereas bag increases the resistance of cells to apoptosis (Farrow and Brown. 1996. *Curr. Opin. Genetics and Devel.* 6:45).

Despite the apparent importance of BCL-x in development and function of T-cells, none of the BCL-x isoforms described so far displays restricted expression with respect to this lineage; all four isoforms of BCL-x are ubiquitously expressed in a wide variety of tissues (Gonzalez-Garcia et al., 1994. *Development* 120, 3033–3042; Fang et al., supra). This may be because previous studies have isolated most of BCL-x isoforms (BCL-xL, BCL-xS and BCL-xΔTM) after screening cDNA libraries from tissues other than T-cells (Gonzalez-Garcia et al., 1994 supra; Fang et al., supra). The physiologic expression of these BCL-x isoforms is not sufficient to confer resistance to apoptosis following TCR ligation, since they are expressed equally well in apoptotic and non-apoptotic T-cell blasts. Moreover, overexpression of Bcl-xL does not affect thymocyte selection (Grillot et al. 1995. *J. Exp. Med.* 182:1973).

SUMMARY OF THE INVENTION

The present invention is based, at least in part, on the discovery of novel molecules, referred to herein as "BCL-xγ" nucleic acid and protein molecules. The BCL-xγ molecules of the present invention are useful as modulating agents in regulating a variety of cellular processes.

Analysis of the BCL-xγ protein indicates that it contains a BH1 and a BH2 domain which are found in other BCL-x family members. However, the BCL-x γ protein also contains a novel γ domain (shown in amino acids 185–235 of SEQ ID NO: 2, which includes an ankyrin domain, e.g., amino acids 185–217 of SEQ ID NO: 2). The γ domain (C-terminal amino acids 185–235) of the deduced BCL-xγ protein lacks homology with the C-termini of previously described murine BCL-xγ isoforms, including BCL-xL, BCL-xβ or BCL-xΔTM. Since BCL-xγ does not contain an apparent hydrophobic domain flanked by charged residues it is unlikely to be membrane-bound, similar to the murine BCL-xΔTM isoform (Gonzalez-Garcia et al., 1994, supra; Fang et al., supra) but in contrast to both, human and murine, BCL-xL and BCL-xS isoforms (Boise et al., 1993) whose C-termini contain sequences that may serve as membrane-anchoring domains (Chen-Levy et al., (1989) *Mol. Cell Biol.* 9, 701–710; Hochenbery et al., 1990 348, 334–336; Nguyen et al., 1993 *J. Biol. Chem.* 268, 25265). The BCL-x γ protein has a calculated molecular weight of approximately 26,122 and migrates at approximately 33 kD. The murine amino acid sequence is shown in Seq. ID No. 2.

In contrast to BCL-xL, BCL-xβ, and BCL-xΔTM, which are expressed in all tissues tested, including brain, eyes, intestine, kidney, liver, lung, lymph nodes, and thymus, the BCL-xγ isoform was detected selectively in thymus, lymph nodes, lung, and eye, but not in heart, intestine, kidney, liver, or brain. BCL-xγ has been found to be expressed only in T-lymphocytes since its message is detected in lymph nodes from BALB/c control but not from BALB/c nu/nu mice or from Rag-2 deficient mice. BCL-xγ is expressed in the less mature, cortisone-sensitive fraction of thymocytes. In addition, BCL-xγ has not been detected in thymuses from class I or class II MHC-deficient B6 mice, implying that expression of this Bcl-x isoform may normally depend on an interaction between the TCR and MHC/peptide complexes. The fact that BCL-xγ has been detected in double positive thymocytes indicates that it plays a role in thymic selection not played by other BCL molecules. Thus, unlike previously described forms of BCL-x molecules, BCL-x γ proteins of the invention are specifically connected to TCR ligation and are essential for resistance to TCR-dependent apoptosis.

In one aspect, the invention features an isolated nucleic acid molecule comprising a nucleotide sequence encoding a naturally occurring BCL-xγ. In one embodiment a BCL-xγ nucleic acid molecule encodes mouse BCL-xγ. In another embodiment a BCL-xγ nucleic acid molecule encodes human BCL-xγ. In a preferred embodiment an isolated BCL-xγ nucleic acid molecule encodes the amino acid sequence of SEQ ID NO: 2.

In one embodiment a BCL-xγ nucleic acid molecule comprises a nucleotide sequence encoding a protein having an amino acid sequence at least 60% homologous to the γ domain shown in amino acids 185–235 of SEQ ID NO: 2 and having anti-apoptotic activity.

In one embodiment a BCL-xγ nucleic acid molecule is at least 92% homologous to the nucleic acid sequence shown in SEQ ID NO:1 or a complement thereof. In a preferred embodiment, a BCL-xγ nucleic acid molecule comprises the sequence shown in SEQ ID NO: 1.

In another embodiment a BCL-xγ nucleic acid molecule encodes an intracellular protein which is anti-apoptotic and has an ankyrin-like domain.

In another embodiment a BCL-xγ nucleic acid molecule comprises a nucleotide sequence at least 80% homologous to the nucleotide sequence shown in nucleotides 930–1082 of SEQ ID NO:1 or a complement thereof.

In another embodiment a BCL-xγ nucleic acid molecule specifically detects a BCL-xγ nucleic acid molecule relative to a nucleic acid molecule encoding another BCL-x molecule. For example, in one embodiment a BCL-xγ nucleic acid molecule hybridizes under stringent conditions to a nucleic acid molecule comprising the nucleotide sequence shown in nucleotides 930–1082 of SEQ ID NO: 1.

In a preferred embodiment an isolated BCL-xγ nucleic acid molecule comprises the coding region of SEQ ID NO: 1 or a complement thereof. In another embodiment a BCL-xγ nucleic acid molecule further comprises nucleotides 1083–1384 of SEQ ID NO:1. In yet another embodiment a BCL-xγ nucleic acid molecule further comprises nucleotides 1–164 of SEQ ID NO:1. In a further embodiment a BCL-xγ nucleic acid molecule further comprises one or more of: domain B, represented by SEQ ID NO:3; domain C, represented by nucleotides 1085–1193 of SEQ ID NO:1; domain D, represented by SEQ ID NO:4; and domain E, represented by nucleotides 1194–1384 of SEQ ID NO:1 downstream of the BCL-xγ coding sequence. In yet another embodiment a nucleic acid molecule of the present invention has a transcriptional regulatory sequence comprising nucleotides 1–164 of SEQ ID NO:1, which may be operatively linked to the BCL-xγ coding sequence or a heterologous coding sequence.

In yet another embodiment the invention provides an isolated nucleic acid molecule which is antisense to the coding strand of a BCL-xγ nucleic acid molecule Another aspect of the invention provides a vector comprising a BCL-xγ nucleic acid molecule. In certain embodiments the vector is a recombinant expression vector. In another embodiment the invention provides a host cell containing a vector of the invention. The invention also provides a method for producing BCL-xγ protein by culturing a host cell of the invention in a suitable medium until BCL-xγ protein is produced.

In another aspect the invention provides isolated or recombinant BCL-xγ proteins. In one embodiment a BCL-xγ protein has an ankyrin-like domain, is intracellular, and is anti-apoptotic. In another embodiment an isolated BCL-xγ protein has (i) an amino acid sequence at least 60% homologous to the γ domain amino acid sequence shown in amino acids 185–235 of SEQ ID NO: 2 and (ii) having anti-apoptotic activity. In a preferred embodiment a BCL-xγ protein has the amino acid sequence of SEQ ID NO: 2. In another embodiment of the invention a BCL-xγ protein is at least about 83.5% homologous to the protein shown in SEQ ID NO:2.

In another embodiment the invention provides a BCL-xγ fusion protein

In another aspect of the invention, antibodies that specifically bind BCL-xγ protein are provided. In one embodiment, the antibodies of the present invention are monoclonal. In another embodiment the subject antibodies are polyclonal.

In another aspect, the invention provides a nonhuman transgenic animal which contains cells carrying a transgene encoding BCL-xγ protein. In one embodiment the transgene alters an endogenous gene encoding endogenous BCL-xγ protein.

In another aspect the present invention provides a method for detecting the presence of BCL-xγ activity in a biological sample by contacting the biological sample with an agent capable of detecting an indicator of BCL-xγ activity such that the presence of BCL-xγ activity is detected in the biological sample. In one embodiment the agent detects BCL-xγ mRNA, e.g., a labeled nucleic acid probe capable of hybridizing to BCL-xγ mRNA. In another embodiment the agent detects BCL-xγ protein, e.g., a labeled antibody that specifically binds to BCL-xγ protein.

In another aspect, the invention provides a method for modulating BCL-xγ activity in a cell comprising contacting the cell with an agent that modulates BCL-xγ activity such that BCL-xγ activity in the cell is modulated. In one embodiment, the agent inhibits BCL-xγ activity. In another embodiment, the agent stimulates BCL-xγ activity. In a preferred embodiment an agent modulates apoptosis in a cell. In one embodiment the agent is an antibody that specifically binds to BCL-xγ protein. In another embodiment the agent modulates transcription of a BCL-xγ gene or translation of a BCL-xγ mRNA. In yet another embodiment, the agent is a nucleic acid molecule having a nucleotide sequence that is antisense to the coding strand of the BCL-xγ mRNA or the BCL-xγ gene.

In one embodiment, the methods of the present invention are used to modulate apoptosis in a T cell. Such methods can be used, e.g., to treat an immune system disorder. In one embodiment BCL-xγ activity is downmodulated to ameliorate an autoimmune disorder. In another embodiment BCL-xγ activity is upmodulated to ameliorate an immunodeficiency.

The present invention also provides a diagnostic assay for identifying a cell or cells at risk for apoptosis in a cell sample, the presence or absence of a genetic lesion characterized by at least one of (i) aberrant modification or mutation of a gene encoding a BCL-xγ protein, and (ii) mis-regulation of said gene; (iii) aberrant post-translational modification of a BCL-xγ protein, wherein a wild-type form of said gene encodes an protein with a BCL-xγ anti-apoptotic activity.

In another aspect the invention provides a method for identifying a compound that modulates the anti-apoptotic activity of a BCL-x γ protein, by providing a indicator composition comprising a BCL-x γ protein having BCL-x γ anti-apoptotic activity, contacting the indicator composition with a test compound, and determining the effect of the test compound on BCL-x γ anti-apoptotic activity in the indicator composition to identify a compound that modulates the anti-apoptotic activity of a BCL-x γ protein.

Other features and advantages of the invention will be apparent from the following detailed description and claims.

BRIEF DESCRIPTION OF THE DRAWINGS

FIG. 1A is the murine cDNA sequence (SEQ ID NO: 1) and predicted protein sequence (SEQ ID NO: 2) of BCL-xγ (GenBank access number U51277).

FIG. 1D is an alignment of BCL-xy C-terminal sequence (residues 185–235 of SEQ ID NO: 2) with an ankyrin-like consensus sequence (SEQ ID NO: 26).

DETAILED DESCRIPTION OF THE INVENTION

Figure 1B:
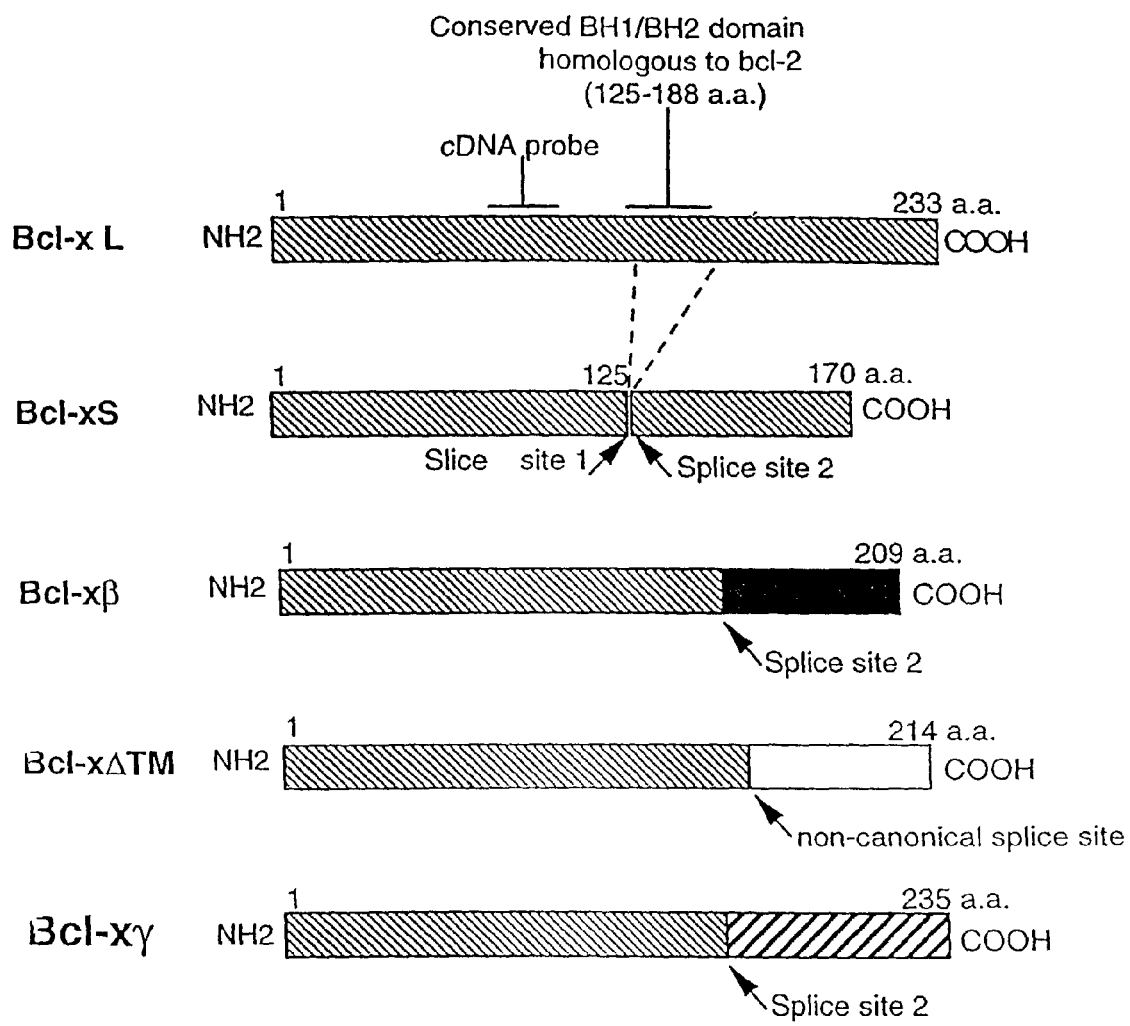
FIG. 1B is a schematic comparison of murine BCL-x isoforms: BCL-xL, BCL-xS, BCL-xβ, BCL-x ΔTM and BCL-xy. Murine Bcl-x isoforms share a long N-terminal region (hatched).

The present invention relates to BCL-xy nucleic acid molecules, proteins, antibodies immunoreactive with BCL-xy proteins, and preparations of such compositions. In addition, drug discovery assays are provided for identifying other agents which can modulate the biological function of BCL-xy proteins. Such agents are useful in modulating growth, differentiation, and survival in a cell. As described herein, BCL-xy modulating agents may be, inter alia, small organic molecules, peptides or peptidomimetics, lipids, carbohydrates, or nucleic acids. Moreover, the present invention provides diagnostic and therapeutic assays and reagents for detecting and treating disorders involving, for example, aberrant expression of mammalian bcl-xγ genes. Other aspects of the invention are described below or will be apparent to those skilled in the art in light of the present disclosure.

I. Isolated Nucleic Acid Molecules

One aspect of the invention pertains to isolated nucleic acid molecules that encode BCL-xγ or biologically active portions thereof, as well as nucleic acid fragments sufficient for use as hybridization probes to identify BCL-xγ-encoding nucleic acid (e.g., BCL-xγ mRNA). As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. For example, in various embodiments, the isolated BCL-xγ nucleic acid molecule may contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a human splenocyte). Moreover, an "isolated" nucleic acid molecule, such as a cDNA molecule, may be free of other cellular material.

In one embodiment an isolated BCL-xy nucleic acid molecule of the invention is a naturally occurring molecule. In a preferred embodiment, an isolated nucleic acid molecule of the invention comprises the nucleotide sequence shown in SEQ ID NO: 1. The sequence of SEQ ID NO: 1 corresponds to the mouse BCL-xγ cDNA. This cDNAs comprises sequences encoding the BCL-xγ protein (i.e., "the coding region", from nucleotides 378–1085 of SEQ ID NO:1), as well as 5' untranslated sequences (nucleotides 1 to 377 of SEQ ID NO:1) and 3' untranslated sequences (nucleotides 1083–1384 of SEQ ID NO:1). Alternatively, the nucleic acid molecule may comprise only the coding region of SEQ ID NO: 1 (e.g., nucleotides 378–1085).

The naturally occurring murine cDNA, comprises unique 3' sequences. The observed sequence variations of the BCL-xγ 3' noncoding region represent the effects of insertions in two locations. The inserted fragments are, fragment B, represented by SEQ ID NO:3; fragment C, represented by nucleotides 1085–1193 of SEQ ID NO:1; fragment D represented by SEQ ID NO:4; and fragment E represented by nucleotides 1194–1384 of SEQ ID NO:1. Four types of 3' UT variants have been defined as follows: (1) A-E; (2) A-C-E; (3) A-B-C-E; and (4) A-C-D-E.

Since all of the sequence variations are located in the 3' noncoding region, these variations do not represent potential artifact products of PCR amplification. Since the length and content of the 3' noncoding region may affect mRNA translational efficiency or stability (Tanguay and Gallie, 1996 *Mol. Cell. Biol.* 16, 146–156), it will, in certain embodiments, be desirable to include portions of the 3' noncoding region. In one embodiment, a BCL-xγ nucleic acid molecule contains all or a portion of the 3' untranslated region of SEQ ID NO:1, e.g., nucleotides 1083–1384. In one embodiment, a BCL-xγ nucleic acid molecule contains a sequence at least about 85% homologous to the sequence shown in nucleotides 1083–1384 SEQ ID NO:1. In another embodiment, a BCL-xγ nucleic acid molecule contains a sequence at least about 90% homologous to the sequence shown in nucleotides 1083–1384 SEQ ID NO:1. In a preferred embodiment, a BCL-xγ nucleic acid molecule contains a sequence at least about 95% homologous to the sequence shown in nucleotides 1083–1384 SEQ ID NO:1.

In certain embodiments, the subject nucleic acid molecule includes one or more of: fragment B, represented by SEQ ID NO:3; fragment C, represented by nucleotides 1085–1193 of SEQ ID NO:1; fragment D represented by SEQ ID NO:4; and fragment E represented by nucleotides 1194–1384 of SEQ ID NO:1. In other embodiments the subject nucleic acid includes the ordered combination of 3' domains selected from the group consisting of: -E, -C-E, -B-C-E, and -C-D-E after the BCL-xγ stop codon.

Transcriptional regulatory sequences can control tissue specific expression of genes. "Transcriptional regulatory sequence" is a term used throughout the specification to refer to DNA sequences, such as initiation signals, enhancers, and promoters, which induce or control transcription of protein coding sequences with which they are operatively linked. In preferred embodiments, transcription of a bcl-xγ gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of BCL-xγ proteins.

In one embodiment a BCL-xγ nucleic acid further contains nucleotides 1–164, i.e., the 5' untranslated region of SEQ ID NO:1. In a particularly preferred embodiment, a bcl-xγ gene is under the control of a transcriptional regulatory sequence which includes nucleotides 1–164 of SEQ ID NO:1. In another embodiment, a BCL-xγ nucleic acid contains a nucleotide sequence at least about 80% homologous to the sequence shown in nucleotides 1–164. In another embodiment, a BCL-xγ nucleic acid contains a nucleotide sequence at least about 85% homologous to the sequence shown in nucleotides 1–164. In a preferred embodiment, a BCL-xγ nucleic acid contains a nucleotide sequence at least about 90% homologous to the sequence shown in nucleotides 1–164. In a particularly preferred embodiment, a BCL-xγ nucleic acid contains a nucleotide sequence at least about 95% homologous to the sequence shown in nucleotides 1–164.

This transcriptional regulatory sequence can also be used as part of a tissue specific promoter to control the transcription of non-bcl-xγ genes, i.e., heterologous genes. As used herein, the term "tissue-specific promoter" means a nucleotide sequence that serves as a promoter, i.e., regulates expression of a selected nucleotide sequence operatively linked to the promoter, and which effects expression of the selected nucleotide sequence in specific cells of a tissue, such as cells of hepatic or pancreatic origin, neuronal cells, or immune cells. The term also covers so-called "leaky" promoters, which regulate expression of a selected nucleic acid primarily in one tissue, but cause expression in other tissues as well. Thus, in one embodiment of the invention a transcriptional regulatory sequence including nucleotides 1–164 of SEQ ID NO:1 is operatively linked to a heterologous coding sequence.

Moreover, the nucleic acid molecule of the invention can comprise only a portion of the coding region of SEQ ID NO:1, for example a fragment encoding a biologically active portion of BCL-xγ. The term "biologically active portion of BCL-xγ" is intended to include portions of BCL-xγ that retain anti-apoptotic activity. The ability of a portion of BCL-xγ to modulate apoptosis can be determined in a number of assays, for example, by measuring the ability of a portion of bcl-x γ to modulate apoptosis after T cell receptor ligation (described further in Example 9). Nucleic acid fragments encoding biologically active portions of BCL-xγ can be prepared by isolating a portion of SEQ ID NO: 1, expressing the encoded portion of BCL-xγ protein or peptide (e.g., by recombinant expression in vitro) and assessing the anti-apoptotic activity of the encoded portion of BCL-xγ protein or peptide.

The BCL-xγ nucleic acid molecule shown in SEQ ID NO:1 was isolated from a mouse thymus cell cDNA library as described in Example 1. Other naturally occurring BCL-xγ nucleic acid molecules, or portions thereof, can be isolated using standard molecular biology techniques and the sequence information provided herein. For example, a human BCL-xγ cDNA can be isolated from a T cell line cDNA library using all or portion of SEQ ID NO: 1 as a hybridization probe and standard hybridization techniques (e.g., as described in Sambrook, J., Fritsh, E. F., and Maniatis, T. *Molecular Cloning: A Laboratory Manual.* 2nd, ed., *Cold Spring Harbor Laboratory,* Cold Spring Harbor, N.Y., 1989). Moreover, a nucleic acid molecule encompassing all or a portion of a nucleic acid molecule homologous to SEQ ID NO: 1 can be isolated by the polymerase chain reaction using oligonucleotide primers designed based upon the sequence of SEQ ID NO: 1. For example, mRNA can be isolated from normal T cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1. For example, primers suitable for amplification of the segment of SEQ ID NO: 1 are shown in SEQ ID NOs: 6 and 7. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a BCL-xγ nucleotide sequence can be prepared by standard synthetic techniques, e.g., using an automated DNA synthesizer.

Preferred BCL-xγ nucleic acid molecules are naturally-occurring nucleic acid molecules. As used herein, a "naturally-occurring" nucleic acid molecule refers to an RNA or DNA molecule having a nucleotide sequence that occurs in nature (e.g., encodes a natural protein). Such, nucleic acid molecules encoding BCL-xγ proteins from other species, and thus which have a nucleotide sequence which differs from the murine sequence of SEQ ID NO: 1, are intended to be within the scope of the invention. In a preferred embodiment, the BCL-xγ nucleic acid molecule of the present invention is isolated from a vertebrate organism. More preferred BCL-xγ nucleic acids are mammalian. Particularly preferred BCL-xγ nucleic acids are human or mouse in origin. In on embodiment, the nucleic acid encodes a natural murine BCL-xy. In a preferred embodiment, a BCL-xγ nucleic acid encodes the protein shown in SEQ ID NO: 2. In another embodiment, the nucleic acid molecule encodes a human homologue of murine BCL-xγ.

In addition to the BCL-xγ nucleotide sequence shown in SEQ ID NO: 1, it will be appreciated by those skilled in the art that DNA sequence polymorphisms that lead to changes in the amino acid sequences of BCL-xy may exist within a population (e.g., the human population). Such genetic polymorphism in the bcl-xγ gene may exist among individuals within a population due to natural allelic variation. Any and all such nucleotide variations and resulting amino acid polymorphisms in BCL-xγ that are the result of natural allelic variation and that do not alter the functional activity of BCL-xγ are intended to be within the scope of the invention.

Nucleic acid molecules corresponding to natural allelic variants and homologues of the BCL-xγ cDNAs of the invention can be isolated based on their homology to the BCL-xγ nucleic acid disclosed herein using the human cDNA, or a portion thereof, as a hybridization probe according to standard hybridization techniques under stringent hybridization conditions. As used herein, the term "hybridizes under stringent conditions" is intended to describe conditions for hybridization and washing under which nucleotide sequences at least 60% homologous to each other typically remain hybridized to each other. Preferably, the conditions are such that at least sequences at least 65%, more preferably at least 70%, and even more preferably at least 75% homologous to each other typically remain hybridized to each other. Such stringent conditions are known to those skilled in the art and can be found in *Current Protocols in Molecular Biology,* John Wiley & Sons, N.Y. (1989), 6.3.1–6.3.6. A preferred, non-limiting example of stringent hybridization conditions are hybridization in 50% formamide in 6× sodium chloride/sodium citrate (SSC) at about 42° C., followed by one or more washes in 0.2×SSC, 0.1% SDS at 50° C. then at 65° C. Preferred probes of the invention are those that hybridize under stringent conditions to the sequence shown in nucleotides 930–1082 of SEQ ID NO: 1. Accordingly, in another embodiment, an isolated nucleic acid molecule of the invention is at least 20 nucleotides in length and hybridizes under stringent conditions to the nucleic acid molecule comprising the nucleotide sequence of SEQ ID NO: 1, preferably to a portion of the sequence shown in nucleotides 930–1082 of SEQ ID NO:1. In other embodiments, the nucleic acid is at least 30, 50, 100, 250, or 500 nucleotides in length. In preferred embodiments, the probe further contains a label group and can be detected, e.g. the label group can be a radioisotope, fluorescent compound, enzyme, or enzyme co-factor. Probes based on the subject BCL-xγ sequences can also be used to detect transcripts or genomic sequences encoding the same or homologous proteins.

In addition to naturally-occurring allelic variants of the bcl-xγ sequence that may exist in the population, the skilled artisan will further appreciate that changes may be introduced by mutation into the nucleotide sequence of SEQ ID NO: 1, thereby leading to changes in the amino acid sequence of the encoded BCL-xγ protein, without altering the functional ability of the BCL-xγ protein. For example, nucleotide substitutions leading to amino acid substitutions at "non-essential" amino acid residues may be made in the sequence of SEQ ID NO: 1. A "non-essential" amino acid residue is a residue that can be altered from the wild-type sequence of BCL-xγ (e.g., the sequence of SEQ ID NO: 2) without altering the anti-apoptotic activity of BCL-xγ, whereas an "essential" amino acid residue is required for BCL-xγ anti-apoptotic activity, e.g., in a thymic cell. Amino acid residues of BCL-xγ that are strongly conserved among members of the BCL family are predicted to be essential in BCL-xγ and thus are not likely to be amenable to significant alteration.

For example, the BCL-xγ proteins of the present invention contain the BH1–4 domains conserved in BCL-2-related proteins (D'Sa-Eipper et al. 1996. *Cancer Res.* 56:3879). Since these domains are conserved among the BCL proteins, they may be less amenable to alteration. In addition, the BCL-xγ proteins of the present invention contain several other structural features, or domains. For example, the γ domain is shown in amino acids 185–235 of SEQ ID NO:2. BCL-x γ is the first protein demonstrated to contain a γ domain sequence. The γ domain does not share a high degree of homology with any known protein. The γ domain does, however, contain a 33 amino acid portion that shows strong homology with the consensus sequence for ankyrin-like domains (Hatada et al., 1992 *Proc. Natl. Acad. Sci. USA* 89, 2489–2493). Since this unique domain is likely responsible for the unique role of BCL-xγ in apoptosis and thymic development, it may be less amenable to manipulation.

In one embodiment a BCL-xγ nucleic acid molecule comprises a nucleotide sequence at least about 80% homologous to nucleotides 930–1082 of SEQ ID NO:1, which encode a γ domain. In a preferred embodiment, a BCL-xγ nucleic acid contains a sequence at least about 90% homologous to nucleotides 930–1082 of SEQ ID NO:1. In another preferred embodiment, a BCL-xγ nucleic acid of the present invention contains a nucleotide sequence at least about 95% homologous to nucleotides 930–1082 of SEQ ID NO:1. In a particularly preferred embodiment, a BCL-xγ nucleic acid contains a nucleotide sequence shown in nucleotides 930–1082 of SEQ ID NO:1.

In another embodiment a BCL-xγ nucleic acid molecule encodes a protein which comprises a sequence at least about 60% homologous to a γ domain shown in amino acids 185–235 of SEQ ID NO:2 and having anti-apoptotic activity. In a preferred embodiment a BCL-xγ nucleic acid molecule encodes a protein which comprises a sequence at least about 70% homologous to a γ domain shown in amino acids 185–235 of SEQ ID NO:2 and having anti-apoptotic activity. In another preferred embodiment a BCL-xγ nucleic acid molecule encodes a protein which comprises a sequence at least about 80% homologous to a γ domain shown in amino acids 185–235 of SEQ ID NO:2 and having anti-apoptotic activity. In yet another preferred embodiment a BCL-xγ nucleic acid molecule encodes a protein which comprises a sequence at least about 90% homologous to a γ domain shown in amino acids 185–235 of SEQ ID NO:2 and having anti-apoptotic activity. In another preferred embodiment a BCL-xγ nucleic acid molecule encodes a protein which comprises a sequence at least about 95% homologous to a γ domain shown in amino acids 185–235 of SEQ ID NO:2 and having anti-apoptotic activity. In a particularly preferred embodiment a BCL-xγ nucleic acid molecule encodes a protein which comprises a sequence shown in amino acids 185–235 of SEQ ID NO:2.

The BCL-xγ protein also has an ankyrin domain. Ankyrin domains define a variety of proteins, including the protooncogene Bcl-3 (Ohno et al., 1990 Cell 60:991), that may use this sequence to bind NF-κB p50 and regulate the activation of this transcription factor ((Hatada et al., 1992 *Proc. Natl. Acad. Sci. USA* 89, 2489–2493)). In one embodiment a BCL-xγ nucleic acid molecule encodes an intracellular protein with a consensus ankyrin domain shown in the sequence NXXXXXXGXTPLXX (SEQ ID NO: 25), which is anti-apoptotic. In a preferred embodiment a BCL-xγ nucleic acid molecule encodes an intracellular protein with the ankyrin domain shown in amino acids 185–217 of SEQ ID NO:2 which is anti-apoptotic.

Another aspect of the invention pertains to nucleic acid molecules encoding BCL-xγ proteins that contain changes in amino acid residues that are not essential for anti-apoptotic activity. Such BCL-xγ proteins differ in amino acid sequence from SEQ ID NO: 2 yet retain anti-apoptotic activity. In one embodiment, the isolated nucleic acid molecule comprises a nucleotide sequence encoding a protein, wherein the protein comprises an amino acid sequence at least 83.5% homologous to the amino acid sequence of SEQ ID NO: 2 and having an anti-apoptotic activity. Preferably, the protein encoded by the nucleic acid molecule is at least 84% homologous to SEQ ID NO: 2, more preferably at least 85% homologous to SEQ ID NO: 2, even more preferably at least 90% homologous to SEQ ID NO: 2 and has anti-apoptotic activity. In a preferred embodiment the protein encoded by the nucleic acid molecule is at least 95% homologous to the amino acid sequence shown in SEQ ID NO:2. A preferred sequence is identical to the sequence shown in SEQ ID NO:2 and has anti-apoptotic activity.

To determine the percent homology of two amino acid sequences (e.g., SEQ ID NO: 2 and a mutant form thereof), the sequences are aligned for optimal comparison purposes (e.g., gaps may be introduced in the sequence of one protein for optimal alignment with the other protein). The amino acid residues at corresponding amino acid positions are then compared. When a position in one sequence (e.g., SEQ ID NO: 2) is occupied by the same or a similar amino acid residue as the corresponding position in the other sequence (e.g., a mutant form of BCL-xγ), then the molecules are homologous at that position (i.e., as used herein amino acid "homology" is equivalent to amino acid identity or similarity). As used herein, an amino acid residue is "similar" to another amino acid residue if the two amino acid residues are members of the same family of residues having similar side chains. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The percent homology between two sequences, therefore, is a function of the number of identical or similar positions shared by two sequences (i.e., % homology=# of identical or similar positions/total # of positions×100).

In a preferred embodiment a BCL-xγ nucleic acid is at least about 92%, 93%, or 94% homologous to the coding sequence shown in SEQ ID NO:1 or its complement. In another preferred embodiment a BCL-xγ nucleic acid is at least about 95% homologous to the coding sequence shown in SEQ ID NO:1 or its complement. In yet another preferred embodiment a BCL-xγ nucleic acid is at least about 97–98% homologous to the coding sequence shown in SEQ ID NO:1. In a preferred embodiment, a BCL-xγ nucleic acid comprises a nucleotide sequence which is identical to the coding sequence of SEQ ID NO: 1.

An isolated nucleic acid molecule encoding a BCL-xγ protein homologous to the protein of SEQ ID NO: 2 can be created by introducing one or more nucleotide substitutions, additions or deletions into the nucleotide sequence of SEQ ID NO: 1 such that one or more amino acid substitutions, additions or deletions are introduced into the encoded protein. Mutations can be introduced into SEQ ID NO: 1 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art, and are defined above. Thus, a predicted nonessential amino acid residue in BCL-xγ is preferably replaced with another amino acid residue from the same side chain family. Alternatively, in another embodiment, mutations can be introduced randomly along all or part of a BCL-xγ coding sequence, such as by saturation mutagenesis, and the resultant mutants can be screened for proteolytic activity to identify mutants that retain proteolytic activity. Following mutagenesis of SEQ ID NO: 1, the encoded protein can be expressed recombinantly (e.g., by transfection as described in Example 9) and the anti-apoptotic activity of the protein can be determined.

A suitable assay for testing the anti-apoptotic activity of portions of BCL-xγ proteins and mutated BCL-xγ proteins is described in detail in Example 9. Briefly, the percentage of cells undergoing apoptosis after T cell receptor ligation can be analyzed using propidium iodide staining. Numerous other methods for measuring apoptosis are known in the art and many assays are commercially available, such as, the DNA fragmentation ELISA, the TUNEL assay, and the apoptotic DNA ladder kit, all from Boehringer Mannheim.

A. Sources of Nucleic Acids

Bcl-xγ nucleic acids can be obtained from mRNA present in any of a number of eukaryotic cells. It should also be possible to obtain nucleic acids encoding mammalian BCL-xγ proteins of the present invention from genomic DNA from both adults and embryos. For example, a gene encoding a BCL-xγ protein can be cloned from either a cDNA or a genomic library in accordance with protocols described herein, as well as those generally known to persons skilled in the art. Examples of tissues and/or libraries suitable for isolation of the subject nucleic acids include T cells, among others. A cDNA encoding a BCL-xγ protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian BCL-xγ protein can also be cloned using established polymerase chain reaction techniques in accordance with the nucleotide sequence information provided by the invention. The nucleic acid of the invention can be DNA or RNA. A preferred nucleic acid is a cDNA represented by a sequence shown in SEQ ID NO: 1.

Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Any of the subject nucleic acids can also be obtained by chemical synthesis. For example, nucleic acids of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988. Nucl. Acids Res. 16:3209). methylphosphonate oligonucleotides can be prepared by use of controlled pore glass polymer supports (Sarin et al., 1988, Proc. Natl. Acad. Sci. U.S.A. 85:7448–7451), etc. Other techniques for chemically synthesizing oligodeoxyribonucleotides and oligoribonucleotides well known in the art such as for example solid phase phosphoramidite chemical synthesis.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

The subject nucleic acids may also contain modified bases. For example, a nucleic acid may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

A modified nucleic acid of the present invention may also include at least one modified sugar moiety selected from the group including but not limited to arabinose, 2-fluoroarabinose, xylulose, and hexose.

In yet another embodiment, the subject nucleic acid may include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

B. Nucleic Acid Probes

In another embodiment a BCL-xγ nucleic acid fragment is an oligonucleotide probe which specifically detects a BCL-xγ nucleic acid relative to another, related BCL nucleic acid. In a preferred embodiment, the subject oligonucleotide hybridizes under stringent conditions to a nucleic acid with at least about 6 consecutive nucleotides encoding a γ domain, for example, nucleotides 930–1082 of SEQ ID NO:1.

In preferred embodiments, the probe further contains a label group and can be detected, e.g. the label group can be a radioisotope, fluorescent compound, enzyme, biotin, or enzyme co-factor. Probes based on the subject BCL-xγ sequences can also be used to detect transcripts or genomic sequences encoding the same or homologous proteins.

C. Antisense Constructs

Another aspect of the invention relates to the use of isolated BCL-xγ nucleic acids in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject BCL-xγ proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a mammalian BCL-xγ protein. Alternatively, the antisense construct is an oligonucleotide probe which is generated ex vivo and which, when introduced into the cell causes inhibition of expression by hybridizing with the mRNA and/or genomic sequences of a mammalian bcl-xγ gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668.

Antisense approaches involve the design of oligonucleotides (either DNA or RNA) that are complementary to BCL-xγ mRNA. The antisense oligonucleotides will bind to the BCL-xγ mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, are preferred. However, sequences complementary to the 3' untranslated sequences of mRNAs may also be used (Wagner, R. 1994. Nature 372:333). Therefore, oligonucleotides complementary to either the 5' or 3' untranslated, non-coding regions of a bcl-xγ gene can be used in an antisense approach to inhibit translation of endogenous BCL-xγ mRNA. Oligonucleotides complementary to the 5' untranslated region of the mRNA preferably include the complement of the AUG start codon. Antisense oligonucleotides complementary to mRNA coding regions may also be used in accordance with the invention. Whether designed to hybridize to the 5', 3' or coding region of BCL-xγ mRNA, antisense nucleic acids should be at least about six nucleotides in length, and are preferably oligonucleotides ranging from 6 to about 50 nucleotides in length. In certain embodiments, the oligonucleotide is at least about 10 nucleotides, at least about 17 nucleotides, at least about 25 nucleotides, or at least about 50 nucleotides.

Regardless of the choice of target sequence, in vitro studies can be performed to quantitate the ability of the antisense oligonucleotide to inhibit gene expression. These studies can utilize controls that distinguish between antisense gene inhibition and nonspecific biological effects of oligonucleotides. Levels of the target RNA or protein can be compared with that of an internal control RNA or protein. Results obtained using the antisense oligonucleotide can be compared with those obtained using a control oligonucleotide. The control oligonucleotide can be approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as: peptides (e.g., for targeting host cell receptors in vivo); or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. W088/09810, published Dec. 15, 1988); or the blood-brain barrier (see, e.g., PCT Publication No. W089/10134, published Apr. 25, 1988); hybridization-triggered cleavage agents; (See, e.g., Krol et al., 1988, BioTechniques 6:958–976); and/or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

While antisense nucleotides complementary to the bcl-xγ coding region sequence can be used, those complementary to the transcribed untranslated region are most preferred. Exemplary antisense oligonucleotides are set forth in SEQ ID NOs. 19, 20, 21, or 22.

The antisense molecules can be delivered to cells which express the BCL-xγ in vivo or in vitro. A number of methods have been developed for delivering antisense DNA or RNA to cells; e.g., antisense molecules can be injected directly into the tissue site, or modified antisense molecules designed to target the desired cells (e.g., antisense linked to peptides or antibodies that specifically bind receptors or antigens expressed on the target cell surface) can be administered systematically.

A preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous BCL-xγ transcripts and thereby prevent translation of the BCL-xγ mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, yeast artifical chromosome, YAC, or viral vector can be used to prepare the recombinant DNA construct which can be introduced directly into the tissue site; e.g., the choroid plexus or hypothalamus. Alternatively, viral vectors can be used which selectively infect the desired tissue (e.g., for brain, herpesvirus vectors may be used), in which case administration may be accomplished by another route (e.g., systemically).

Ribozyme molecules designed to catalytically cleave BCL-xγ mRNA transcripts can also be used to prevent translation of BCL-xγ mRNA and expression of BCL-xγ. (See, e.g., PCT International Publication WO90/11364, published Oct. 4, 1990; Sarver et al., 1990, Science 247: 1222–1225). While ribozymes that cleave mRNA at site specific recognition sequences can be used to destroy BCL-xγ mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are numerous potential hammerhead ribozyme cleavage sites within the nucleotide sequence of BCL-xγ cDNA. Preferably, the ribozyme is engineered so that the cleavage recognition site is located near the 5' end of the BCL-xγ specific mRNA; i.e., to increase efficiency and minimize the intracellular accumulation of non-functional mRNA transcripts.

Ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in BCL-xγ mRNA.

As in the antisense approach, the ribozymes can be composed of modified oligonucleotides (e.g. for improved stability, targeting, etc.) and should be delivered to cells which express the BCL-xγ in vivo e.g., T cells or thymocytes. A preferred method of delivery involves using a DNA construct "encoding" the ribozyme under the control of a strong constitutive promoter such as the pol III or pol II promoter, so that transfected cells will produce sufficient quantities of the ribozyme to destroy endogenous BCL-xγ and inhibit translation. Because ribozymes unlike antisense molecules, are catalytic, a lower intracellular concentration is required for efficiency.

Endogenous bcl-xγ gene expression can also be reduced by inactivating or "knocking out" the bcl-xγ gene or its promoter using targeted homologous recombination. (e.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional bcl-xγ (or a completely unrelated DNA sequence) flanked by DNA homologous to the endogenous bcl-xγ gene (either the coding regions or regulatory regions of the bcl-xγ gene) can be used, with or without a selectable marker and/or a negative selectable marker, to transfect cells that express BCL-xγ in vivo. Insertion of the DNA construct, via targeted homologous recombination, results in inactivation of the bcl-xγ gene. Such approaches are particularly suited in the generation of animal offspring with an inactive BCL-xγ (e.g., see Thomas & Capecchi 1987 and Thompson 1989, supra). However this approach can be adapted for use in humans provided appropriate delivery means are used.

Alternatively, endogenous bcl-xγ gene expression can be reduced by targeting deoxyribonucleotide sequences complementary to the regulatory region of the bcl-xy gene (i.e., the bcl-xy promoter and/or enhancers) to form triple helical structures that prevent transcription of the bcl-xγ gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich. region of a single strand of the duplex in a parallel orientation to that strand. In addition, nucleic acid molecules may be chosen that are purine-rich. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Exemplary modified bases are set forth above.

D. Modifications to Nucleic Acids

Modifications to nucleic acid molecules of the invention can be introduced as a means of increasing intracellular stability and half-life. Modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. Modified bases are known in the art and are described above.

II. Expression Vectors and Host Cells

The present invention also provides for vectors containing the subject nucleic acid molecules. As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions.

This invention also provides expression vectors containing a nucleic acid encoding a BCL-xγ protein, operatively linked to at least one transcriptional regulatory sequence. "Operatively linked" is intended to mean that the nucleotide sequence is linked to a regulatory sequence in a manner which allows expression of the nucleotide sequence. Transcriptional regulatory sequences are art-recognized and are selected to direct expression of the subject mammalian BCL-xγ proteins. Exemplary regulatory sequences are described in Goeddel; Gene Expression Technology: Methods in Enzymology 185, Academic Press, San Diego, Calif. (1990).

In a preferred embodiment the expression vector of the present invention is capable of replicating in a cell. In one embodiment, the expression vector includes a recombinant gene encoding a peptide having BCL-xγ anti-apoptotic activity. Such expression vectors can be used to transfect cells and thereby produce proteins, including fusion proteins, encoded by nucleic acids as described herein. Moreover, the gene constructs of the present invention can also be used as a part of a gene therapy protocol to deliver nucleic acids encoding either an agonistic or antagonistic form of one of the subject mammalian BCL-xγ proteins. Thus, another aspect of the invention features expression vectors for in vivo or in vitro transfection and expression of a mammalian BCL-xγ protein in particular cell types so as to reconstitute the function of, or alternatively, abrogate the function of BCL-xγ in a tissue. This could be desirable when treating a disorder, for example, resulting from the misexpression of BCL-xγ in a tissue.

In addition to viral transfer methods, such as those described above, non-viral methods can also be employed to cause expression of a subject BCL-xγ protein in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject BCL-xγ protein gene by the targeted cell. Exemplary targeting means of this type include liposomal derived systems, poly-lysine conjugates, and artificial viral envelopes.

The recombinant bcl-xγ genes can be produced by ligating nucleic acid encoding a BCL-xγ protein, or a portion thereof, into a vector suitable for expression in either prokaryotic cells, eukaryotic cells, or both. Expression vectors for production of recombinant forms of the subject BCL-xγ proteins include plasmids and other vectors. For instance, suitable vectors for the expression of a BCL-xγ protein include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a BCL-xγ protein is produced recombinantly utilizing an expression vector generated by sub-cloning the coding sequence of one of the bcl-xγ genes represented in SEQ ID NO:1.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant BCL-xγ protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In some cases it will be desirable to express only a portion of a BCL-xγ protein. The subject vectors can also include fragments of a BCL-xγ nucleic acid encoding a fragment of a BCL-xγ protein, preferably a fragment having anti-apoptotic activity.

The subject vectors can be used to transfect a host cell in order to express a recombinant form of the subject BCL-xγ proteins. The host cell may be any prokaryotic or eukaryotic cell. Thus, a nucleotide sequence derived from the cloning of mammalian BCL-xγ proteins, encoding all or a selected portion of the full-length protein, can be used to produce a recombinant form of a mammalian BCL-xγ protein in a cell.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The present invention further pertains to methods of producing the subject BCL-xγ proteins. For example, a host cell transfected with a nucleic acid vector directing expression of a nucleotide sequence encoding the subject proteins can be cultured under appropriate conditions to allow expression of the peptide to occur. The cells may be harvested, lysed and the protein isolated. A cell culture includes host cells, media and other byproducts. Suitable media for cell culture are well known in the art. The recombinant BCL-xγ protein can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant BCL-xγ protein is a fusion protein containing a domain which facilitates its purification, such as GST fusion protein or poly(His) fusion protein.

In other embodiments transgenic animals, described in more detail below can be used to produce recombinant proteins.

The present invention also provides for a recombinant transfection system, including a bcl-xγ gene construct operatively linked to a transcriptional regulatory sequence and a gene delivery composition for delivering the gene construct to a cell so that the cell expresses the BCL-xγ protein.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian BCL-xγ protein or, in the case of anti-sense expression from the transferred gene, the expression of a naturally-occurring form of the BCL-xγ protein is disrupted.

A "delivery composition" shall mean a targeting means (e.g. a molecule that results in higher affinity binding of a gene, protein, protein or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors).

III. Proteins

The present invention further pertains to isolated and/or recombinant forms of a BCL-xγ protein.

The term "recombinant protein" refers to a protein of the present invention which is produced by recombinant DNA techniques, wherein generally, DNA encoding a mammalian BCL-xγ protein is inserted into a suitable expression vector which is in turn used to transform a host cell to produce the heterologous protein, as described above. Moreover, the phrase "derived from", with respect to a recombinant bcl-xγ gene, is meant to include within the meaning of "recombinant protein" those proteins having an amino acid sequence of a natural occurring BCL-xγ protein, or a similar amino acid sequence which is generated by mutations including substitutions and deletions (including truncation) of a naturally occurring form of the protein.

The present invention also makes available isolated BCL-xγ proteins which are isolated from, or otherwise substantially free from other cellular proteins, especially other factors which may normally be associated with the BCL-xγ protein. The term "substantially free of other cellular proteins" (also referred to herein as "contaminating proteins") or "substantially pure or purified preparations" are defined as encompassing preparations of BCL-xγ proteins having less than about 20% (by dry weight) contaminating protein, and preferably having less than about 5% contaminating protein. Functional forms of the subject proteins can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least about 80% by dry weight, more preferably in the range of 95–99% by weight, and most preferably at least about 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" are not meant to encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified BCL-xγ preparations will lack any contaminating proteins from the same animal from which BCL-xγ is normally produced, as can be accomplished by recombinant expression of, for example, a human BCL-xγ protein in a non-human cell.

In a preferred embodiment a BCL-xγ protein includes the amino acid sequence shown in SEQ ID NO:2. In other embodiments, a BCL-xγ protein is capable of modulating apoptosis in a T cell.

The present invention also provides for BCL-xγ proteins which have amino acid sequences evolutionarily related to the BCL-xγ proteins represented in SEQ ID NO: 2. In a preferred embodiment, a BCL-xγ protein of the present invention is a mammalian BCL-xγ protein. The term "evolutionarily related to", with respect to amino acid sequences of mammalian BCL-xγ proteins, refers to both proteins having amino acid sequences which have arisen naturally, and also to mutational variants of mammalian BCL-xγ proteins which are derived, for example, by combinatorial mutagenesis. Such related BCL-xγ proteins preferred by the present invention are at least about 83.5% homologous with the amino acid sequence shown in SEQ ID NO: 2. In other embodiments, a BCL-xγ protein is at least about 85% homologous with the amino acid sequence shown in SEQ ID NO: 2. In a preferred embodiment, a BCL-xγ protein is at least about 90% homologous with the amino acid sequence shown in SEQ ID NO: 2. In another preferred embodiment, a BCL-xγ protein is at least about 95% homologous with the amino acid sequence shown in SEQ ID NO: 2.

In certain embodiments, it will be advantageous to alter a BCL-xγ protein to provide homologs of one of the subject BCL-xγ proteins which would function in some capacity as either a BCL-xγ agonist (mimetic) or a BCL-xγ antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of BCL-xγ proteins.

Homologs of each of the subject BCL-xγ proteins can be generated by mutagenesis, such as by discrete point mutation(s), or by truncation. For instance, mutation can give rise to homologs which retain substantially the same, or merely a subset, of the biological activity of the BCL-xγ protein from which it was derived. Alternatively, antagonistic forms of the protein can be generated which are able to inhibit the function of the naturally occurring form of the protein, such as by competitively binding to a BCL-xγ binding protein. In addition, agonistic forms of the protein may be generated which are constitutively active. Thus, the mammalian BCL-xγ protein and homologs thereof provided by the subject invention may be either positive or negative regulators of apoptosis.

The recombinant BCL-xγ proteins of the present invention include homologs of the wild type BCL-xγ proteins, such as versions of those protein which are resistant to proteolytic cleavage, as for example, due to mutations which alter ubiquitination or other enzymatic targeting associated with the protein. The subject proteins can also be glycosylated. A "glycosylated" BCL-xγ protein is an BCL-xγ protein having a covalent linkage with a glycosyl group (e.g. a derivatized with a carbohydrate). An unglycosylated BCL-xγ protein can be generated by expression in a system which is defective for glycosylation, such as a bacterial cell. Alternatively, an existing glycosylation site can be mutated to preclude carbohydrate attachment. Likewise, new glycosylation sites, such as for N-linked or O-linked glycosylation, can be added by recombinant techniques.

BCL-xγ proteins may also be chemically modified to create BCL-xγ derivatives by forming covalent or aggregate conjugates with other chemical moieties, such as lipids, phosphate, acetyl groups and the like. Covalent derivatives of BCL-xγ proteins can be prepared by linking the chemical moieties to functional groups on amino acid sidechains of the protein or at the N-terminus or at the C-terminus of the protein.

Modification of the structure of the subject mammalian BCL-xγ proteins can be for such purposes as enhancing therapeutic or prophylactic efficacy, stability (e.g., ex vivo shelf life and resistance to proteolytic degradation in vivo), or post-translational modifications (e.g., to alter phosphorylation pattern of the protein). Such modified peptides, when designed to retain at least one activity of the naturally-occurring form of the protein, or to produce specific antagonists thereof, are considered functional equivalents of the BCL-xγ proteins described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W H Freeman and Co.: 1981). Whether a change in the amino acid sequence of a peptide results in a functional BCL-xγ homolog (e.g. functional in the sense that the resulting protein mimics or antagonizes the wild-type form) can be readily determined by assessing the ability of the variant peptide to produce a response in cells in a fashion similar to the wild-type protein as discussed herein, or competitively inhibit such a response. Proteins in which more than one replacement has taken place can readily be tested in the same manner.

In another embodiment, a BCL-xγ protein is encoded by a BCL-xγ nucleic acid as defined herein.

Full length proteins or fragments corresponding to one or more particular motifs and/or domains or to arbitrary sizes, for example, at least about 5, 10, 25, 50, 75, 100, 125, 150 amino acids in length are within the scope of the present invention. For example, isolated BCL-xγ proteins can include all or a portion of an amino acid sequence corresponding to a BCL-xγ protein represented in or homologous to SEQ ID NO:2. Isolated peptidyl portions of BCL-xγ proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a BCL-xγ protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "naturally occurring") BCL-xγ protein.

In another embodiment, an isolated or recombinant BCL-xγ protein includes a sequence corresponding to a γ domain (i.e., amino acids 185–235 of SEQ ID NO:2) and having at least about 60% homology to that sequence and has anti-apoptotic activity. In yet another embodiment, an isolated or recombinant BCL-xγ protein includes a sequence at least about 70% homologous to a γ domain of a BCL-xγ protein and has anti-apoptotic activity. In a preferred embodiment, an isolated or recombinant BCL-xγ protein includes a sequence at least about 80% homologous to a γ domain of a BCL-xγ protein and has anti-apoptotic activity. In another preferred embodiment, an isolated or recombinant BCL-xγ protein includes a sequence at least about 90% homologous to a γ domain of a BCL-xγ protein and has anti-apoptotic activity. In a particularly preferred embodiment an isolated or recombinant BCL-xγ protein includes a γ domain of a BCL-xγ protein such as that shown in SEQ ID NO:2 amino acids 185–235 and has anti-apoptotic activity.

In another embodiment, a BCL-xγ nucleic acid molecule encodes an intracellular protein containing an ankyrin-like domain which is anti-apoptotic. In one embodiment, a BCL-xγ nucleic acid molecule encodes an intracellular protein with a consensus ankyrin domain shown in the sequence NXXXXXXGXTPLXX (SEQ ID NO: 25) which is anti-apoptotic. In a preferred embodiment, a BCL-xγ nucleic acid molecule encodes a protein with the ankyrin domain shown in amino acids 185–217 of SEQ ID NO:2, and which is intracellular and anti-apoptotic.

In certain preferred embodiments, the invention features a purified or recombinant BCL-xγ protein having a calculated molecular weight of approximately 26,122 kD. It will be understood that certain post-translational modifications can increase the apparent molecular weight of the BCL-xγ protein relative to the unmodified polypeptide chain. The BCL-xγ protein migrates with an apparent molecular weight of 33,000 kD.

This invention further provides a method for generating sets of combinatorial mutants of the subject BCL-xγ proteins as well as truncation mutants, and is especially useful for identifying potential variant sequences (e.g. homologs) that modulate a BCL-xγ bioactivity. The purpose of screening such combinatorial libraries is to generate, for example, novel BCL-xγ homologs which can act as either agonists or antagonist, or alternatively, possess novel activities all together. To illustrate, combinatorially-derived homologs can be generated to have an increased potency relative to a naturally occurring form of the protein.

Likewise, BCL-xγ homologs can be generated by the present combinatorial approach to selectively inhibit (antagonize) naturally occurring BCL-xγ. Moreover, manipulation of certain domains of BCL-xγ by the present method can provide domains more suitable for use in fusion proteins.

In one embodiment, a variegated library of BCL-xγ variants is generated by combinatorial mutagenesis at the nucleic acid level, and is encoded by a variegated gene library. For instance, a mixture of synthetic oligonucleotides can be enzymatically ligated into gene sequences such that the degenerate set of potential BCL-xγ sequences are expressible as individual polypeptides, or alternatively, as a set of larger fusion proteins (e.g. for phage display) containing the set of BCL-xγ sequences therein.

There are many ways by which such libraries of potential BCL-xγ homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential BCL-xγ sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a BCL-xγ clone in order to generate a variegated population of BCL-xγ fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a bcl-xγ coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of BCL-xγ homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates isolation of the vector encoding the gene whose product was detected. Each of the illustrative assays described below are amenable to high through-put analysis as necessary to screen large numbers of degenerate BCL-xγ sequences created by combinatorial mutagenesis techniques.

In one embodiment, cell based assays can be exploited to analyze the variegated BCL-xγ library. For instance, the library of expression vectors can be transfected into a T cell line, preferably a T cell line that does not express BCL-xγ. The transfected cells are then treated to induce apoptosis, e.g., with anti-CD3, and the effect of the BCL-xγ mutant can be detected, e.g. cell viability. Plasmid DNA can then be recovered from the cells which score for inhibition, or alternatively, potentiation of a BCL-xγ activity, and the individual clones further characterized.

Combinatorial mutagenesis has a potential to generate very large libraries of mutant proteins, e.g., in the order of $10^{26}$ molecules. Combinatorial libraries of this size can be screened using a variety of techniques, e.g., recrusive ensemble mutagenesis (REM) (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention also provides for reduction of the mammalian BCL-xγ proteins to generate mimetics, e.g. peptide or non-peptide agents, which are able to disrupt binding of a mammalian BCL-xγ protein of the present invention with binding proteins or interactors. Thus, such mutagenic techniques as described above are also useful to map the determinants of the BCL-xγ proteins which participate in protein-protein interactions. Such interactions can be involved in, for example, binding of the subject mammalian BCL-xγ protein to proteins which may function upstream (including both activators and repressors of its activity) or downstream of the BCL-xγ protein, whether they are positively or negatively regulated by it. To illustrate, the critical residues of a subject BCL-xγ protein which are involved in molecular recognition of interactor proteins upstream or downstream of a BCL-xγ (such as, for example BH1 domains, BH2 domains, or ankyrin binding domains) can be determined and used to generate BCL-xγ-derived peptidomimetics which competitively inhibit binding of the naturally occurring BCL-xγ protein to that moiety. By employing, for example, scanning mutagenesis to map the amino acid residues of each of the subject BCL-xγ proteins which are involved in binding other extracellular proteins, peptidomimetic modulating agents can be generated which mimic those residues of the BCL-xγ protein which facilitate the interaction. Such mimetics may then be used to interfere with the normal function of a BCL-xγ protein. For example, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted γ lactani rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun126:419; and Dann et al. (1986) Biochem Biophys Res Commun 134:71).

In another embodiment, the coding sequences for the protein can be incorporated as a part of a fusion gene including a nucleotide sequence encoding a different protein to generate a fusion protein or chimeric protein.

A "chimeric protein" or "fusion protein" is a fusion of a first amino acid sequence encoding one of the subject mammalian BCL-xγ proteins with a second amino acid sequence defining a domain (e.g. protein portion) foreign to and not substantially homologous with any domain of one of the mammalian BCL-xγ proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-BCL-xγ-Y, wherein BCL-xγ represents a portion of the protein which is derived from one of the mammalian BCL-xγ proteins, and X and Y are independently absent or represent amino acid sequences which are not related to one of the mammalian BCL-xγ sequences in an organism, including naturally occurring mutants.

Fusion proteins can also facilitate the expression of proteins, and accordingly, can be used in the expression of the mammalian BCL-xγ proteins of the present invention. For example, BCL-xγ proteins can be generated as glutathione-S-transferase (GST-fusion) proteins. Such GST-fusion proteins can enable easy purification of the BCL-xγ protein, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different protein sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

In preferred embodiments, fusion proteins of the present invention contain a detectable label or a matrix binding domain.

The preparation of fusion proteins is often desirable when producing an immunogenic fragment of a BCL-xγ protein. For example, the VP6 capsid protein of rotavirus can be used as an immunologic carrier protein for portions of the BCL-xγ protein, either in the monomeric form or in the form of a viral particle. The nucleic acid sequences corresponding to the portion of a subject BCL-xγ protein to which antibodies are to be raised can be incorporated into a fusion gene construct which includes coding sequences for a late vaccinia virus structural protein to produce a set of recombinant viruses expressing fusion proteins comprising BCL-xγ epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a BCL-xγ protein and the poliovirus capsid protein can be created to enhance immunogenicity of the set of polypeptide antigens (see, for example, EP Publication NO: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a BCL-xγ protein is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of BCL-xγ proteins can also be expressed and presented by bacterial cells.

IV. Antibodies.

Another aspect of the invention pertains to an antibody specifically reactive with a mammalian BCL-xγ protein. For example, by using immunogens derived from a BCL-xγ protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian BCL-xγ protein or an antigenic fragment which is capable of eliciting an antibody response, or a fusion protein as described above). Techniques for conferring immunogenicity on a protein or peptide include conjugation to carriers or other techniques well known in the art. An immunogenic portion of a BCL-xγ protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a BCL-xγ protein of a mammal, e.g. antigenic determinants of a protein represented by SEQ ID NO:2.

Following immunization of an animal with an antigenic preparation of a BCL-xγ polypeptide, anti-BCL-xγ antisera can be obtained and, if desired, polyclonal anti-BCL-xγ antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian BCL-xγ protein of the present invention and monoclonal antibodies isolated from a culture comprising such hybridoma cells.

As an alternative to preparing monoclonal antibody-secreting hybridomas, a monoclonal anti-BCL-xγ antibody can be identified and isolated by screening a recombinant combinatorial immunoglobulin library (e.g., an antibody phage display library) with BCL-xγ to thereby isolate immunoglobulin library members that bind BCL-xγ. Kits for generating and screening phage display libraries are commercially available (e.g., the Pharmacia *Recombinant Phage*

*Antibody System,* Catalog No. 27-9400-01; and the Stratagene *SurfZAP™ Phage Display Kit,* Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-BCL-xγ antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol* 141:4053–4060.

The term antibody as used herein is intended to include fragments thereof which are also specifically reactive with one of the subject mammalian BCL-xγ proteins. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a BCL-xγ protein conferred by at least one CDR region of the antibody.

Antibodies which specifically bind BCL-xγ epitopes can also be used in immunohistochemical staining of tissue samples in order to evaluate the abundance and pattern of expression of each of the subject BCL-xγ proteins. Anti-BCL-xγ antibodies can be used diagnostically in immuno-precipitation and immuno-blotting to detect and evaluate BCL-xγ protein levels in tissue as part of a clinical testing procedure. Likewise, the ability to monitor BCL-xγ protein levels in an individual can allow determination of the efficacy of a given treatment regimen for an individual afflicted with such a disorder. Diagnostic assays using anti-BCL-xγ antibodies can include, for example, immunoassays designed to aid in early diagnosis of a degenerative disorder, particularly ones which are manifest at birth. Diagnostic assays using anti-BCL-xγ protein antibodies can also include immunoassays designed to aid in early diagnosis and phenotyping neoplastic or hyperplastic disorders.

Another application of anti-BCL-xγ antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a BCL-xγ protein, e.g. other orthologs of a particular BCL-xγ protein or other paralogs from the same species, can then be detected with antibodies, as, for example, reacting nitrocellulose filters lifted from infected plates with anti-BCL-xγ antibodies. Positive phage detected by this assay can then be isolated from the infected plate. Thus, the presence of BCL-xγ homologs can be detected and cloned from other animals, as can alternate isoforms (including splicing variants) from humans.

In certain embodiments, it will be desirable to attach a label group to the subject antibodies to facilitate detection. One means for labeling an anti-BCL-xγ protein specific antibody is via linkage to an enzyme and use in an enzyme immunoassay (EIA) (Voller, "The Enzyme Linked Immunosorbent Assay (ELISA)", Diagnostic Horizons 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

It is also possible to label the antibody with a fluorescent compound. When the fluorescently labeled antibody is exposed to light of the proper wave length, its presence can then be detected. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

V. Methods of the Invention

Drug Screening Assays

The present invention provides for assays which can be used to screen for modulating agents, including BCL-xγ homologs, which are either agonists or antagonists of the normal cellular function of the subject BCL-xγ polypeptides. For example, the invention provides a method in which an indicator composition is provided which has a BCL-xγ protein having BCL-xγ anti-apoptotic activity. The indicator composition can be contacted with a test compound. The effect of the test compound on BCL-xγ anti-apoptotic activity, as measured by a change in the indicator composition, can then be determined to thereby identify a compound that modulates the anti-apoptotic activity of a BCL-xγ protein. A statistically significant change, such as a decrease or increase, in the level of BCL-xγ anti-apoptotic activity in the presence of the test compound (relative to what is detected in the absence of the test compound) is indicative of the test compound being a BCL-xγ modulating agent. The indicator composition can be, for example, a cell or a cell extract. In one embodiment, BCL-xγ anti-apoptotic activity is assessed as described in Example 9.

In many drug screening programs which test libraries of modulating agents and natural extracts, high throughput assays are desirable in order to maximize the number of modulating agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test modulating agent. Moreover, the effects of cellular toxicity and/or bioavailability of the test modulating agent can be generally ignored in the in vitro system, the assay instead being focused primarily on the effect of the drug on the molecular target as may be manifest in an alteration of binding affinity with upstream or downstream elements.

In an exemplary screening assay of the present invention, the modulating agent of interest is cotacted with interactor proteins which may function upstream (including both activators and repressors of its activity) or to proteins which may function downstream of the BCL-xγ protein, whether they are positively or negatively regulated by it. To the mixture of the modulating agent and the upstream or downstream element is then added a composition containing a BCL-xγ protein. Detection and quantification of the interaction of BCL-xγ with it's upstream or downstream elements provide a means for determining a modulating agent's efficacy at inhibiting (or potentiating) complex formation between BCL-xγ and the BCL-xγ-binding elements. The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The efficacy of the modulating agent can be assessed by generating dose response curves from data obtained using various concentrations of the test modulating agent. Moreover, a control assay can also be performed to provide a baseline for comparison. In the control assay, isolated and purified BCL-xγ protein is added to a composition containing the BCL-xγ-binding element, and the formation of a complex is quantitated in the absence of the test modulating agent.

Complex formation between the BCL-xγ protein and a BCL-xγ binding element may be detected by a variety of techniques. Modulation of the formation of complexes can be quantitated using, for example, detectably labeled proteins such as radiolabeled, fluorescently labeled, or enzymatically labeled BCL-xγ proteins, by immunoassay, or by chromatographic detection.

Typically, it will be desirable to immobilize either BCL-xγ or its binding protein to facilitate separation of complexes from uncomplexed forms of one or both of the proteins, as well as to accommodate automation of the assay. Binding of BCL-xγ to an upstream or downstream element, in the presence and absence of a candidate agent, can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase/BCL-xγ (GST/BCL-xγ) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test modulating agent, and the mixture incubated under conditions conducive to complex formation, e.g., at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of BCL-xγ-binding protein found in the bead fraction quantitated from the gel using standard electrophoretic techniques such as described in the appended examples.

Other techniques for immobilizing proteins on matrices are also available for use in the subject assay. For instance, either BCL-xγ or its cognate binding protein can be immobilized utilizing conjugation of biotin and streptavidin. For instance, biotinylated BCL-xγ molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with BCL-xγ but which do not interfere with binding of upstream or downstream elements can be derivatized to the wells of the plate, and BCL-xγ trapped in the wells by antibody conjugation. As above, preparations of a BCL-xγ-binding protein and a test modulating agent are incubated in the BCL-xγ-presenting wells of the plate, and the amount of complex trapped in the well can be quantitated. Exemplary methods for detecting such complexes, in addition to those described above for the GST-immobilized complexes, include immunodetection of complexes using antibodies reactive with the BCL-xγ binding element, or which are reactive with BCL-xγ protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the BCL-xγ-BP. To illustrate, the BCL-xγ-BP can be chemically cross-linked or genetically fused with horseradish peroxidase, and the amount of protein trapped in the complex can be assessed with a chromogenic substrate of the enzyme, e.g. 3,3'-diamino-benzadine terahydrochloride or 4-chloro-1-napthol. Likewise, a fusion protein comprising the protein and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-BCL-xγ antibodies, can be used. Alternatively, the protein to be detected in the complex can be "epitope tagged" in the form of a fusion protein which includes, in addition to the BCL-xγ sequence, a second protein for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J).

In addition to cell-free assays, such as described above, the readily available source of mammalian BCL-xγ proteins provided by the present invention also facilitates the generation of cell-based assays for identifying small molecule agonists/antagonists and the like. For example, cells can be caused to overexpress a recombinant BCL-xγ protein in the presence and absence of a test modulating agent of interest, with the assay scoring for modulation in BCL-xγ responses by the target- cell mediated by the test agent. As with the cell-free assays, modulating agents which produce a statistically significant change in BCL-xγ-dependent responses (either inhibition or potentiation) can be identified. In an illustrative embodiment, the expression or activity of a BCL-xγ is modulated in cells and the effects of modulating agents of interest on the readout of interest (such as apoptosis) are measured. For example, the expression of genes which are up- or down-regulated in response to a T cell receptor-mediated signal cascade can be assayed. In preferred embodiments, the regulatory regions of such genes, e.g., the 5' flanking promoter and enhancer regions, are operatively linked to a marker (such as luciferase) which encodes a gene product that can be readily detected.

Monitoring the influence of modulating agents on cells may be applied not only in basic drug screening, but also in clinical trials. In such clinical trials, the expression of a panel of genes may be used as a "read out" of a particular drug's therapeutic effect.

In another aspect of the invention, the subject BCL-xγ proteins can be used to generate a "two hybrid" assay (see, for example, U.S. Pat. No. 5,283,317; Zervos et al. (1993) Cell 72:223–232; Madura et al. (1993) J Biol Chem 268: 12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with BCL-xγ ("BCL-xγ-binding proteins" or "BCL-xγ-bp"). Such BCL-xγ-binding proteins would likely be regulators of BCL-xγ bioactivity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a BCL-xγ protein. The second hybrid protein encodes a transcriptional activation domain fused in frame to a sample gene from a cDNA library. If the bait and sample hybrid proteins are able to interact, e.g., form a BCL-xγ-dependent complex, they bring into close proximity the DNA binding domain and the activation domain of the transcriptional activator. This proximity is sufficient to cause transcription of a reporter gene which is operatively linked to a transcriptional regulatory site responsive to the transcriptional activator, and expression of the reporter gene can be detected and used to score for the interaction of the BCL-xγ and sample proteins.

Diagnostic and Prognostic Assays

The present method provides a method for determining if a subject is at risk for a disorder characterized by aberrant cell proliferation or apoptosis. In preferred embodiments, the methods can be characterized as comprising detecting, in a sample of cells from the subject, the presence or absence of a genetic lesion characterized by at least one of (i) an alteration affecting the integrity of a gene encoding a BCL-xγ-protein, or (ii) the misregulation or (iii) aberrant post-translational modification of the bcl-xγ gene. To illustrate, such genetic lesions can be detected by ascertaining the existence of at least one of (i) a deletion of one or more nucleotides from a bcl-xγ gene, (ii) an addition of one or more nucleotides to a bcl-xγ gene, (iii) a substitution of one or more nucleotides of a bcl-xγ gene, (iv) a gross chromosomal rearrangement of a BCL-xγ gene, (v) a gross alteration in the level of a messenger RNA transcript of a bcl-xγ gene, (vii) aberrant modification of a BCL-xγ gene, such as of the methylation pattern of the genomic DNA, (vii) the presence of a non-wild type splicing pattern of a messenger RNA transcript of a bcl-xγ gene, (viii) a non-wild type level of a BCL-xγ-protein, (ix) allelic loss of a bcl-xγ gene, and (x) inappropriate post-translational modification of a BCL-xγ-protein. As set out below, the present invention provides a large number of assay techniques for detecting lesions in a bcl-xγ gene, and importantly, provides the ability to discern between different molecular causes underlying BCL-xγ-dependent aberrant cell growth, proliferation and/or differentiation.

As discussed in more detail below, the probes of the present invention can also be used as a part of a diagnostic test kit for identifying cells or tissue which misexpress a BCL-xγ protein, such as by measuring a level of a BCL-xγ-encoding nucleic acid in a sample of cells from a patient; e.g. detecting BCL-xγ mRNA levels or determining whether a genomic bcl-xγ gene has been mutated or deleted. Briefly, nucleotide probes can be generated from the subject bcl-xγ genes which facilitate histological screening of intact tissue and tissue samples for the presence (or absence) of BCL-xγ-encoding transcripts. Similar to the diagnostic uses of anti-BCL-xγ antibodies (described in detail below), the use of probes directed to BCL-xγ messages, or to genomic bcl-xγ sequences, can be used for both predictive and therapeutic evaluation of allelic mutations which might be manifest in certain disorders. Used in conjunction with immunoassays as described herein, the oligonucleotide probes can help facilitate the determination of the molecular basis for a disorder which may involve some abnormality associated with expression (or lack thereof) of a BCL-xγ protein. For instance, variation in polypeptide synthesis can be differentiated from a mutation in a coding sequence.

In an exemplary embodiment, a nucleic acid composition is provided which contains an oligonucleotide probe previously described. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the bcl-xγ-gene (see Abravaya et al. (1995) Nuc Acid Res 23:675–682). In an illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a bcl-xγ gene under conditions such that hybridization and amplification of the bcl-xγ-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In another embodiment of the subject assay, mutations in a bcl-xγ gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the bcl-xγ gene and detect mutations by comparing the sequence of the sample BCL-xγ with the corresponding wild-type (control) sequence. Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). Any of a variety of automated sequencing procedures may be utilized when performing the subject assays (Biotechniques (1995) 19:448), including by sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one skilled in the art that, for certain embodiments, the occurrence of only one, two or three of the nucleic acid bases need be determined in the sequencing reaction. For instance, A-tract sequencing where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type BCL-xγ sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in BCL-xγ cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a BCL-xγ sequence, e.g., a wild-type BCL-xγ sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in bcl-xγ genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) Mutat Res 285:125–144; and Hayashi (1992) *Genet Anal Tech Appl* 9:73–79). Single-stranded DNA fragments of sample and control BCL-xγ nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition, it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a BCL-xγ gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant BCL-xγ proteins, which are discussed, above, may also be used in disease diagnostics and prognostics. Such diagnostic methods, may be used to detect abnormalities in the level of BCL-xγ protein expression, or abnormalities in the structure and/or tissue, cellular, or subcellular location of BCL-xγ protein. Structural differences may include, for example, differences in the size, electronegativity, or antigenicity of the mutant BCL-xγ protein relative to the normal BCL-xγ protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of BCL-xγ proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the BCL-xγ protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Moreover, any of the above methods for detecting alterations in a bcl-xγ gene or gene product can be used to monitor the course of treatment or therapy.

Modulation of BCL-xγ Activity

Yet another aspect of the invention pertains to methods of modulating BCL-xγ activity in a cell. The modulatory methods of the invention involve contacting the cell with an agent that modulates BCL-xγ activity such that BCL-xγ activity in the cell is modulated. The agent may act by modulating the activity of BCL-xγ protein in the cell or by modulating transcription of the BCL-xγ gene or translation of the BCL-xγ mRNA. As used herein, the term "modulating" is intended to include inhibiting or decreasing BCL-xγ activity and stimulating or increasing BCL-xγ activity. Accordingly, in one embodiment, the agent inhibits BCL-xγ activity. An inhibitory agent may function, for example, by directly inhibiting BCL-xγ anti-apoptotic activity or by modulating a signaling pathway which negatively regulates BCL-xγ. In another embodiment, the agent stimulates BCL-xγ activity. A stimulatory agent may function, for example, by directly stimulating BCL-xγ anti-apoptotic activity, or by modulating a signaling pathway that leads to stimulation of BCL-xγ activity.

A. Inhibitory Agents

According to one modulatory method of the invention, BCL-xγ activity is inhibited in a cell by contacting the cell with an inhibitory agent. Inhibitory agents of the invention can be, for example, intracellular binding molecules that act to inhibit the expression or activity of BCL-xγ. As used herein, the term "intracellular binding molecule" is intended to include molecules that act intracellularly to inhibit the expression or activity of a protein by binding to the protein itself, to a nucleic acid (e.g., an mRNA molecule) that encodes the protein or to a second protein with which the first protein normally interacts (e.g., a BCL-xγ binding protein). Examples of intracellular binding molecules, described in further detail below, include antisense BCL-xγ nucleic acid molecules (e.g., to inhibit translation of BCL-xγ mRNA), intracellular anti-BCL-xγ antibodies (e.g., to inhibit the activity of BCL-xγ protein), and dominant negative mutants of the BCL-xγ protein.

In one embodiment, an inhibitory agent of the invention is an antisense nucleic acid molecule that is complementary to a gene encoding BCL-xγ, or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316–318; Bennett, M. R. and Schwartz, S. M. (1995) Circulation 92:1981–1993; Mercola, D. and Cohen, J. S. (1995) Cancer Gene Ther. 2:47–59; Rossi, J. J. (1995) Br. Med. Bull. 51:217–225; Wagner, R. W. (1994) Nature 372:333–335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA. An antisense nucleic acid for inhibiting the expression of BCL-xγ protein in a cell can be designed based upon the nucleotide sequence encoding the BCL-xγ protein (e.g., SEQ ID NO: 1 or a portion thereof), constructed according to the rules of Watson and Crick base pairing.

An antisense nucleic acid can exist in a variety of different forms. For example, the antisense nucleic acid can be an oligonucleotide that is complementary to only a portion of a BCL-xγ gene. Antisense oligonucleotides can be constructed using chemical synthesis procedures known in the art. An antisense oligonucleotide can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit BCL-xγ expression in cells in culture, one or more antisense oligonucleotides can be added to cells in culture media, typically at about 200 mg oligonucleotide/ml.

Alternatively, an antisense nucleic acid can be produced biologically using an expression vector into which a nucleic acid has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. For example, for inducible expression of antisense RNA, an inducible eukaryotic regulatory system, such as the Tet system (e.g., as described in Gossen, M. and Bujard, H. (1992) Proc. Natl. Acad. Sci. USA 89:5547–5551; Gossen, M. et al. (1995) Science 268:1766–1769; PCT Publication No. WO 94/29442; and PCT Publication No. WO 96/01313) can be used. The antisense expression vector is prepared as described above for recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique, as described above for recombinant expression vectors.

In another embodiment, an antisense nucleic acid for use as an inhibitory agent is a ribozyme. Ribozymes are catalytic RNA molecules with ribonuclease activity which are capable of cleaving a single-stranded nucleic acid, such as an mRNA, to which they have a complementary region (for reviews on ribozymes see e.g., Ohkawa, J. et al. (1995) *J. Biochem.* 118:251–258; Sigurdsson, S. T. and Eckstein, F. (1995) *Trends Biotechnol.* 13:286–289; Rossi, J. J. (1995) *Trends Biotechnol.* 13:301–306; Kiehntopf, M. et al. (1995) *J. Mol. Med.* 73:65–71). A ribozyme having specificity for BCL-xγ mRNA can be designed based upon the nucleotide sequence of the BCL-xγ cDNA. For example, a derivative of a Tetrahymena L-19 IVS RNA can be constructed in which the base sequence of the active site is complementary to the base sequence to be cleaved in a BCL-xγ mRNA. See for example U.S. Pat. Nos. 4,987,071 and 5,116,742, both by Cech et al. Alternatively, BCL-xγ mRNA can be used to select a catalytic RNA having a specific ribonuclease activity from a pool of RNA molecules. See for example Bartel, D. and Szostak, J. W. (1993) *Science* 261: 1411–1418.

Another type of inhibitory agent that can be used to inhibit the expression and/or activity of BCL-xγ in a cell is an intracellular antibody specific for the BCL-xγ protein. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274: 193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al. (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204: 666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of BCL-xγ activity according to the inhibitory methods of the invention, an intracellular antibody that specifically binds the BCL-xγ protein is expressed in the cytoplasm of the cell. To prepare an intracellular antibody expression vector, antibody light and heavy chain cDNAs encoding antibody chains specific for the target protein of interest, e.g., BCL-xγ, are isolated, typically from a hybridoma that secretes a monoclonal antibody specific for the BCL-xγ protein. Hybridomas secreting anti-BCL-xγ monoclonal antibodies, or recombinant anti-BCL-xγ monoclonal antibodies, can be prepared as described above. Once a monoclonal antibody specific for BCL-xγ protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit BCL-xγ activity in a cell, the expression vector encoding the anti-BCL-xγ intracellular antibody is introduced into the cell by standard transfection methods, as discussed hereinbefore.

Other inhibitory agents that can be used to inhibit the activity of a BCL-xγ protein are chemical compounds that inhibit BCL-xγ anti-apoptotic activity. Such compounds can be identified using screening assays that select for such compounds, as described herein. Additionally or alternatively, compounds that inhibit BCL-xγ anti-apoptotic activity can be designed using approaches known in the art.

B. Stimulatory Agents

According to another modulatory method of the invention, BCL-xγ activity is stimulated in a cell by contacting the cell with a stimulatory agent. Examples of such stimulatory agents include active BCL-xγ protein and nucleic acid molecules encoding BCL-xγ that are introduced into the cell to increase BCL-xγ activity in the cell. A preferred stimulatory agent is a nucleic acid molecule encoding a BCL-xγ protein, wherein the nucleic acid molecule is introduced into the cell in a form suitable for expression of the active BCL-xγ protein in the cell. To express a BCL-xγ protein in a cell, typically a BCL-xγ cDNA is first introduced into a recombinant expression vector using standard molecular biology techniques, as described herein. A BCL-xγ cDNA can be obtained, for example, by amplification using the polymerase chain reaction (PCR) or by screening an appropriate cDNA library as described herein. Following isolation or amplification of BCL-xγ cDNA, the DNA fragment is introduced into an expression vector and transfected into target cells by standard methods, as described herein.

Other stimulatory agents that can be used to stimulate the activity of a BCL-xγ protein are chemical compounds that stimulate BCL-xγ activity in cells, such as compounds that enhance BCL-xγ anti-apoptotic activity. Such compounds can be identified using screening assays that select for such compounds, as described in detail above.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (i.e., cultured) in vitro with a modulatory agent of the invention to modulate BCL-xγ activity in the cells. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells can be enriched for example, by positive selection using antibodies to T cell surface markers, for example by incubating cells with a specific primary monoclonal antibody (mAb), followed by isolation of cells that bind the mAb using magnetic beads coated with a secondary antibody that binds the primary mAb. Specific cell populations (e.g., T cells) can also be isolated by fluorescence activated cell sorting according to standard methods. Monoclonal antibodies to T cell-specific surface markers known in the art and many are commercially available. If desired, cells treated in vitro with a modulatory agent of the invention can be readministered to the subject. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

For practicing the modulatory method in vivo in a subject, the modulatory agent can be administered to the subject such that BCL-xγ activity in cells of the subject is modulated. The term "subject" is intended to include living organisms in which an immune response can be elicited. Preferred subjects are mammals. Examples of subjects include humans, monkeys, dogs, cats, mice, rats, cows, horses, goats and sheep.

For stimulatory or inhibitory agents that comprise nucleic acids (including recombinant expression vectors encoding BCL-xγ protein, antisense RNA, intracellular antibodies or dominant negative inhibitors), the agents can be introduced into cells of the subject using methods known in the art for introducing nucleic acid (e.g., DNA) into cells in vivo. Examples of such methods encompass both non-viral and viral methods, including:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxypropyl-3-dimethylhydroxyethylammonium bromide (DMRIE) and dioleoyl phosphatidylethanolamine (DOPE) (see e.g., Logan, J. J. et al. (1995) *Gene Therapy* 2:38–49; San, H. et al. (1993) *Human Gene Therapy* 4:781–788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψcrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868, 116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA*

89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

A modulatory agent, such as a chemical compound that modulates the BCL-xγ anti-apoptotic activity, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described herein.

There are a wide variety of pathological conditions for which BCL-xγ modulating agents of the present invention can be used in treatment. In one embodiment, such agents modulate apoptosis in a cell. In a further embodiment this method can be used to treat a subject suffering from a disorder which would benefit from the modulation of apoptosis. In a preferred embodiment, BCL-xγ is modulated to enhance apoptosis of a T cell, such as to promote the negative selection of autoreactive T cells. In another preferred embodiment, BCL-xγ is modulated to suppress apoptosis in a T cell, such as in the promotion of T cell survival in HIV infected T cells.

Other exemeplary disorders for which modulation of BCL-xγ can be used in treatment include, but are not limited to, various immune-mediated disorders. The term disorder is meant to include both normal conditions that would benefit from an alteration in BCL-xγ activity and various disease states.

Since the subject BCL-xγ modulating agents can either increase or decrease BCL-xγ activity, the agents will be useful for both stimulating or suppressing immune responses.

In certain cases, the subject modulating agents can also be used to inhibit responses in clinical situations where it is desirable to downmodulate T cell survival. For example, it may be desirable to downmodulate BCL-xγ activity to promote T cell apoptosis, thus limiting T cell responsiveness in certain disorders. Examples include: graft-versus-host disease, cases of transplantation, and autoimmune diseases (including, for example, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions,leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis). Downmodulation of BCL-xγ will also be desirable in cases of allergy such as, atopic allergy.

Conversely, it will be desirable to upregulate BCL-xγ activity to treat immunodeficiency diseases, such as primary immunodeficiencies (including, severe combined immunodeficiency, adenosine deaminase deficiency, purine nucleoside phosphorylase deficiency, MHC class II deficiency, reticular dysgenesis, X-linked agammaglobulinemia, X-linked hypogammaglobulinemia, Ig deficiency with increased IgM, Ig heavy chain-gene deletions, k-chain deficiency IgA deficiency, selective deficiency of IgG subclass, common variable immunodeficiency, transient hypogammaglobulinemia of infancy, Wiskott-Aldrich syndrome, ataxia telangiectasia, DiGeorge syndrome, Bloom syndrome, Fanconi anemia, and Down syndrome-related immunodeficiency, as well as other syndromes associated with immunodeficiency) and immunodeficiencies resulting from other causes, such as HIV disease/AIDS.

Additionally, it may be desirable to upregulate BCL-xγ activity to increase T cell survival in the case of other disorders. For example, cellular responses to tumors, or pathogens, such as viruses, bacteria, fungi, parasites and the like, may be enhanced and/or prolonged, by promoting T cell survival, thus enhancing T cell responses with the subject modulating agents.

VI. Pharmaceutical Preparations

The subject modulating agents can be administered to a subject at therapeutically effective doses to treat or ameliorate a disorder benefiting from the modulation of BCL-xγ. The data obtained from cell culture assays and animal studies can be used in formulating a range of dosages for use in humans. The dosage of such modulating agents lies preferably within a range of circulating or tissue concentrations that include the ED50 with little or no toxicity. The dosage may vary within this range depending upon the dosage form employed and the route of administration utilized. For any modulating agent used in the method of the invention, the therapeutically effective dose can be estimated initially from cell culture assays. A dose may be formulated in animal models to achieve a circulating plasma concentration range that includes the IC50 (i.e., the concentration of the test modulating agent which achieves a half-maximal inhibition of symptoms) as determined in cell culture. Such information can be used to more accurately determine useful doses in humans. Levels in plasma may be measured, for example, by high performance liquid chromatography.

In clinical settings, the gene delivery systems for the therapeutic bcl-xγ gene can be introduced into a patient by any of a number of methods, each of which is familiar in the art. For example, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A mammalian bcl-xγ gene, such as represented in SEQ ID NO:1, or a sequence homologous thereto can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g., retroviral vectors, the pharmaceutical preparation can comprise one or more cells which produce the gene delivery system.

Pharmaceutical preparations for use in accordance with the present invention may also be formulated in conventional manner using one or more physiologically acceptable carriers or excipients. Thus, the modulating agents and their physiologically acceptable salts and solvates may be formulated for administration by, for example, injection, inhalation or insufflation (either through the mouth or the nose) or oral, buccal, parenteral or rectal administration.

For such therapy, the modulating agents of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical preparations may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active modulating agent.

For administration by inhalation, the preparations for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the modulating agent and a suitable powder base such as lactose or starch.

The modulating agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The modulating agents may also be formulated in rectal compositions such as suppositories or retention enemas, e.g., containing conventional suppository bases such as cocoa butter or other glycerides.

In addition to the formulations described previously, the modulating agents may also be formulated as a depot preparation. Such long acting formulations may be administered by implantation (for example subcutaneously or intramuscularly) or by intramuscular injection. Thus, for example, the modulating agents may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

The compositions may, if desired, be presented in a pack or dispenser device, or as a kit with instructions. The composition may contain one or more unit dosage forms containing the active ingredient. The pack may for example comprise metal or plastic foil, such as a blister pack. The pack or dispenser device may be accompanied by instructions for administration.

VII. Transgenic Animals

The present invention also provides for transgenic animals in which expression of a genomic sequence or cDNA encoding a functional BCL-xγ protein is enhanced, induced, disrupted, prevented or suppressed. The transgenic animals produced in accordance with the present invention will include exogenous genetic material. As set out above, the exogenous genetic material will, in certain embodiments, be a DNA sequence which results in the production of a BCL-xγ protein (either agonistic or antagonistic), an antisense transcript, or a BCL-xγ mutant. Further, in such embodiments, the sequence will be attached to a transcriptional control element, e.g., a promoter, which preferably allows the expression of the transgene product in a specific type of cell.

As used herein, the term "transgene" means a nucleic acid sequence (whether encoding or antisense to one of the mammalian BCL-xγ proteins), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the mammalian BCL-xγ proteins, e.g., either agonistic or antagonistic forms. However, transgenic animals in which the recombinant bcl-xγ gene is silent are also contemplated, as for example, the FLP or CRE recombinase dependent constructs described below. Moreover, "transgenic animal" also includes those recombinant animals in which gene disruption of one or more bcl-xγ genes is caused by human intervention, including both recombination and antisense techniques.

The "non-human animals" of the invention include mammals such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that one of the recombinant mammalian bcl-xγ genes is present and/or expressed or disrupted in some tissues but not others.

These systems may be used in a variety of applications. For example, the cell- and animal-based model systems may be used to further characterize bcl-xγ genes and proteins. In addition, such assays may be utilized as part of screening strategies designed to identify modulating agents which are capable of ameliorating disease symptoms. Thus, the animal- and cell-based models may be used to identify drugs, pharmaceuticals, therapies and interventions which may be effective in treating disease.

One aspect of the present invention concerns transgenic animals which are comprised of cells (of that animal) which contain a transgene of the present invention and which preferably (though optionally) express an exogenous BCL-xγ protein in one or more cells in the animal. A bcl-xγ transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a BCL-xγ protein can be essential for many forms of lineage analysis and can additionally provide a means to assess the effects of, for example, lack of BCL-xγ expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject BCL-xγ proteins. For example, excision of a target sequence which interferes with the expression of a recombinant bcl-xγ gene, such as one which encodes an antagonistic homolog or an antisense transcript, can be designed to activate expression of that gene. This interference with expression of the protein can result from a variety of mechanisms, such as spatial separation of the bcl-xγ gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251: 1351–1355; PCT publication WO 92/15694) can be used to generate in vivo site-specific genetic recombination systems.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant BCL-xγ protein can be regulated via control of recombinase expression.

Use of the cre/loxP recombinase system to regulate expression of a recombinant BCL-xγ protein requires the construction of a transgenic animal containing transgenes encoding both the Cre recombinase and the subject protein. Animals containing both the Cre recombinase and a recombinant bcl-xγ gene can be provided through the construction of "double" transgenic animals. A convenient method for providing such animals is to mate two transgenic animals each containing a transgene, e.g., a bcl-xγ gene and recombinase gene.

One advantage derived from initially constructing transgenic animals containing a bcl-xγ transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic bcl-xγ transgene is silent will allow the study of progeny from that founder in which disruption of BCL-xγ mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the bcl-xγ transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a bcl-xγ transgene could remain silent into adulthood until "turned on" by the introduction of the trans-activator.

In one embodiment, gene targeting, which is a method of using homologous recombination to modify an animal's genome, can be used to introduce changes into cultured embryonic stem cells. By targeting a bcl-xγ gene of interest e.g., in embryonic stem (ES) cells, these changes can be introduced into the germlines of animals to generate chimeras. The gene targeting procedure is accomplished by introducing into tissue culture cells a DNA targeting construct that includes a segment homologous to a target bcl-xγ locus, and which also includes an intended sequence modification to the bcl-xγ genomic sequence (e.g., insertion, deletion, point mutation). The treated cells are then screened for accurate targeting to identify and isolate those which have been properly targeted.

Methods of culturing cells and preparation of knock out constructs for insertion are known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current Topics in Devel. Biol. 20:357–371); and by Hogan et al. (Manipulating the Mouse Embryo: A Laboratory Manual, Cold Spring Harbor Laboratory Press, Cold Spring Harbor, N.Y. [1986]).

Introduction of the transgenic constructs nucleotide sequence into the embryo may be accomplished by any means known in the art such as, for example, microinjection, electroporation, calcium phosphate, or lipofection. Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264).

Other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a bcl-xγ-gene can be controlled by recombinase sequences.

Animals containing more than one knockout construct and/or more than one transgene expression construct are prepared in any of several ways. A preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The contents of all cited references, including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The present invention is further illustrated by the following examples which should not be construed as limiting in any way.

Example 1

Cloning of the BCL-x γ Gene from a T-Cell-Derived DNA Library

A thymus λ ZapII cDNA library derived from BALB/cJ mice (Stratagene, La Jolla Calif.) was screened with a $^{32}$P-labeled 60 mer oligonucleotide (5'-GGGGTGATGTG-GAGCTGGGATGTCAGGTCACTGAATGC-CCGCCGGTACCGCA GTTCAAAC-3', SEQ ID NO:5) derived from a human bcl-x cDNA sequence (base pairs 423–483) homologous to the region of chicken bcl-x (Boise et al. 1993 Cell 74, 597–608) by hybridization to approximately 10[6] phages blotted on 20 filters in duplicates according to a modification of the protocols by Wood et al. (1985. Proc. Natl. Acad. Sci. USA 82:1585) and Jacobs et al. (1988 Nucleic Acids Res. 16, 4637–4650). Briefly, the filters were prehybridized for 2 hours and hybridized overnight in 6×NaCl/Cit, 5× Denhardt's solution containing boiled sonicated salmon sperm DNA at 0.1 mg/ml at 42° C. The filters were rinsed three times with 6×NaCl/Cit at 4° C. and washed twice for 30 mm with 6×NaCl/Cit at 4° C. The filters were then rinsed with th Me$_4$NCl (tetramethylammonium chloride) wash solution including 50 mM Tris-Cl, pH 8.0, 2 mM EDTA and 0.1% SDS at 37° C., 45° C., 50° C., 55° C., 60° C., 65° C. and 70° C. respectively for 20 mm at each temperature. Six clones were isolated and purified (Bclx 5,6,7,8,10,11); four contained inserts of the same length and sequenced and corresponded to Bcl-xL cDNA and a fifth to Bcl-xβ (GenBank accession numbers U51279, U51278) (M. Gonzalez-Garcia, et al., Development 120, 3033 (1994), W. Fang, J. J. Rivard, D. L. Mueller, T. W. Bebrens, J. Immunol. 153, 4388 (1994). Sequencing was done by double-stranded DNA dideoxy chain termination method using T7 DNA polymerase (US Biochem). Sequencing was performed twice on both strands by walking along the cDNAs with primers custom-synthesized by Amitof (Cambridge, Mass.). Other DNA manipulations were performed according to standard protocols (Sambrook et al., 1989 Molecular Cloning. A laboratory manual 2nd edition. Cold Spring Harbour Laboratory Press).

One clone, termed Bclx7 (GenBank accession number U51277), contained a 1384 bp insert comprised of a 5' noncoding region of 377 nucleotides, an ORF of 708 nucleotides and a 3' noncoding region of 299 nucleotides (FIG. 1A). This represented a novel isoform of the Bcl-x gene in which the 3' region of Bcl-xL was replaced by a 144 bp sequence which predicts a unique C-terminus of 47 amino acids (FIG. 1A). This insert did not represent a cloning artifact because the novel 144 bp subsequence begins precisely at a conserved donor/acceptor splice site used by murine and human Bcl-x isoforms (L. H. Boise et al., Cell 74, 597 (1993), M. Gonzalez-Garcia, et al., Development 120, 3033 (1994), W. Fang, J. J. Rivard, D. L. Mueller, T. W. Behrens, J. Immunol. 153, 4388 (1994) (FIG. 1B) and the sequence was independently cloned from thymocyte RNA (using a primer specific for a conserved region of murine Bcl-x and a Bcl-x-7 specific primer. The recovered thymic sequence was identical to the cDNA insert isolated from the λ Zap II cDNA library and the new isoform was designated bcl-xγ.

Example 2.

PCR Cloning of the bcl-xγ Gene

Total RNA was extracted from murine thymus (BALB/c) after homogenization with a Brinkmann homogenizer (Brinkmann Instruments, New York). Reverse transcription/PCR was performed on a GeneAmp PCR 9600 (Perkin-Elmer using a GeneAmp RNA-PCR kit (Perkin-Elmer Cetus) typically at 42° C. for 30 min, 99° C. for 5 min and 4° C. for 5 min, according to the manufacturer's protocols. All oligonucleotide primers were synthesized by Amitof (Cambridge Mass.). For PCR cloning, one primer specific for the 5' upstream bcl-x common region (5'-<u>TCGCTCGCCCACA</u>TCCCAGCTTCACATAACCCC-3', SEQ ID NO:6) (Note: underlining in original) and a second primer specific for the 3' downstream bcl-xγ region (5'-<u>CTGGTTCGGCCCA</u>CGTCCTTCCTGAAGT-CCTCC-3', SEQ ID NO:7) (Note: underlining in original) were used (underlining indicates regions specific for PCR-Direct™ cloning kit [Clontech]). Amplification products were separated on agarose gels, purified with Geneclean II kit (Bio101), subcloned into the PCR-Direct™ vector and sequenced by the chain termination method.

Example 3

In Vitro Transcription and Translation of bcl-xγ

Figure 2:
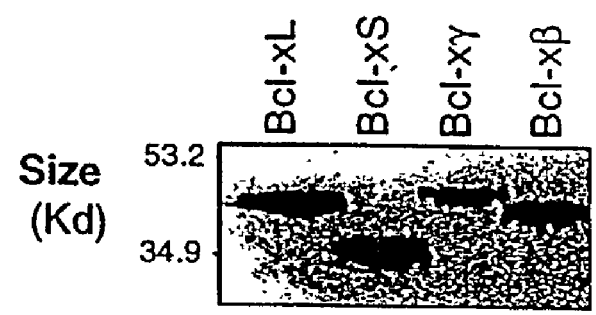
FIG. 2 shows SDS page analysis of protein products of BCL-xL, BCL-xS, BCL-xβ and BCL-xy after in vitro transcription and translation.

In vitro transcription and translation assays using linearized recombinant bcl-x plasmids were performed to confirm the length of the ORF deduced from the cDNA sequence of bcl-xγ (FIG. 2). Recombinant plasmid bluescripts containing cDNAs from bcl-xL, bcl-xS, bcl-x-β and bcl-xγ were linearized with a unique PstI restriction enzyme at the 3' end of the insert and polycloning sites of plasmid. In vitro transcription and translation, using the linearized recombinant bluescript as template, were performed using a TNT T7/T3-coupled reticulocyte lysate system, according to the manufacturer's protocol (Promega). Briefly, 1 μg of linearized plasmid in which T7 promoter sequence was located upstream of the cDNA insert of bcl-x isoforms was added into 50 μl of TNT reticulocyte lysate supplemented with T7 RNA polymerase, RNAase inhibitor, $^{35}$S-methionine, and a mixture of other amino acids. After incubation for 90 min at 30° C., 10 μl of each newly-synthesized $^{35}$S-methionine labeled protein were analyzed by a 12% SDS polyacrylamide gel electrophoresis and autoradiography. The apparent size of BCL-xγ protein after in vitro transcription/translation is consistent with the size predicted from its open reading frame, since the BCL-xγ protein product migrates at a position similar to BCL-xL (233 a.a. residues) (FIG. 1B) and more slowly than the BCL-xβ protein (209 a.a.) and the BCL-xS (170 a.a.). Molecular weight standards (kDa) are indicated on the left margin of the figure.

Figure 1C:
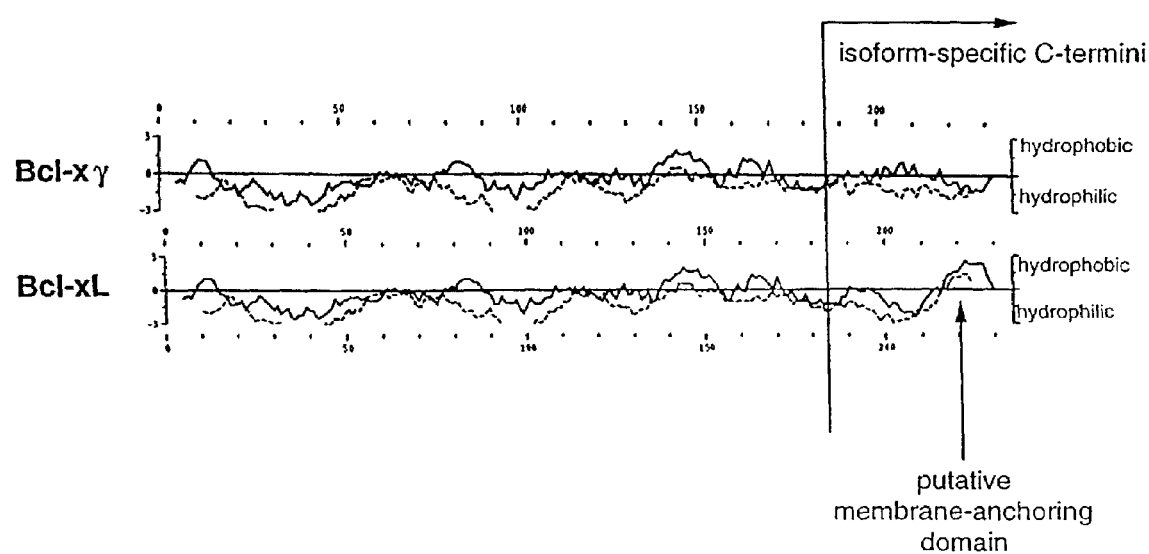
FIG. 1C is a hydrophobicity plot of BCL-xL and BCL-xy.

As expected from the predicted bcl-xγ ORF of 708 nt/235 aa, the apparent size of the translated Bcl-xγ protein was slightly larger than the (233 aa) BCL-xL protein product and considerably larger than both the (170 aa) Bcl-xS (W. Fang, J. J. Rivard, D. L. Mueller, T. W. Bebrens, *J. Immunol.* 153, 4388 (1994) and the (209 aa) BCL-xβ proteins (M. Gonzalez-Garcia, et al., *Development* 120, 3033 (1994). Analysis of the hydrophobicity of the unique C-terminus of the BCL-xγ protein indicated that BCL-xγ lacks an obvious hydrophobic domain flanked by charged residues (FIG. 1C), which are present in human and murine BCL-xL and BCL-xS (L. H. Boise et al., *Cell* 74, 597 (1993), D. Hockenberry, G. Nunez, C. Milliman, R. D. Schreiber, S. J. Korsmeyer, *Nature* 348, 334 (1990); M. Nguyen, D. G. Millar, V. W. Yong, S. J. Korsmeyer, G. C. Shore, . *J. Biol. Chem.* 268, 25265 (1993). Hydrophobicity of BCL-xL and BCL-xγ was calculated using the GCG program based on Goldman's (solid line) or Kyte-Doolittle's (dashed line) algorithm. A 33 aa region within the C-terminal domain of BCL-xγ showed strong homology with the consensus sequence of ankyrin-like domains (FIG. 1D, the consensus sequence of ankyrin-like domain which spans 33 amino acid residues in different species is shown) that are embedded in a number of intracellular proteins including BCL-3, which uses this subsequence to bind to NF-κB p50 (H. N. Hatada et al., *Proc. Natl. Acad. Sci. USA* 89, 2489 (1992).

Example 4

Gene Expression in Prokaryotic Cells as Fusion Protein

BCL-xγ has been successfully expressed in *E. coli*. The bcl-xγ cDNA was amplified by PCR using primer 5'-CCGG-GAATTCATCTCAGAGCAACCGGGAGCTGGTG-3' (SEQ ID NO:8), specific for the BCL-x common region, and a second primer 5'-CCAGGAATTCGGATCCCGTCCTTC-CTGAAGTCCTCCT-3', (SEQ ID NO:9), specific for the unique region of bcl-xγ, which contain an EcoRi endonuclease restriction site, respectively. These primers flank the 5' and 3' ends of the full mature bcl-xγ open reading frame. The amplified DNA has been purified, cut with EcoRI and ligated into the EcoRI site of pGEX-3X, a high expression prokaryotic vector and *E. coli* DH5α strain has been transformed. Ampicillin resistant colonies were screened for the synthesis of GST-BCL-x γ fusion protein by SDS-PAGE. Recombinant protein was purified from bacterial lysate by affinity chromatography on glutathione-agarose resin.

Example 5

Measurement of Gene Expression by RT/PCR

In addition to the bcl-xγ specific primer set, a primer containing a 3' unique region of bcl-xL and bcl-xS (5'-CCACCAACAAGACAGGCT-3', SEQ ID NO:10) was used to pair with the 5' primer from the bcl-x common region for amplification of the bcl-xL fragment. Similarly, a primer called DTM1 (5'-CTCTCCTCCCTCACACACCCCTCTC-3', SEQ ID NO:11) complementary to the 3' specific region of Bcl-xΔTM and a primer called 3ep (5' AAGATACAG-GTCCCTTAAA-3', SEQ ID NO:12) complementary to the 3' specific region of bcl-xβ were used to pair with the 5' primer from the bcl-x common region for amplification of bcl-xΔTM and bcl-xβ. A pair of primers specific for mouse β-actin (5'-ATGGATGACGATATCGCTGC-3'(SEQ ID NO:13) and 5'-CTAGAAGCACTTGCGGTGCAC-3', SEQ ID NO:14) was used as an internal control for RT-PCR to evaluate usage of comparable amounts of cDNA in all samples. Furthermore, in activated O3 clones primers for interleukin-2 (5'-TTCAAGCTCCACTTCAAGCTC-3'(SEQ ID NO:15) and 5'-GACAGAAGGCTATCCATCTCC-3', SEQ ID NO:16) and interferon-γ (5'-TGCATCTTG-GCTTTGCAGCTCTTCCTCATG-3'(SEQ ID NO:17) and 5'-TGGACCTGTGGGTTGTTGACCTCAAACTTG-3', SEQ ID NO:18) served as controls for efficient stimulation. PCR reactions were typically performed through 35–45 cycles using Taq DNA polymerase (Perkin-Elmer) supplemented with TaqStart antibody in order to maintain the specificity of amplified fragments (Clontech). Each 3-step thermal cycle consisted of 30 seconds at 94° C., 30 seconds at 60° C., 30 seconds at 72° C. To encompass the exponential phase of the amplification, 25 μl of the reaction mix was removed at regular intervals during PCR, as previously described (Moore et al., 1994 *Immunology* 81, 115–119). A negative control containing all reagents except cDNA was included in each PCR analysis (Moore et al., 1995 *J. Immunol.* 155, 4653–4660). PCR fragments in 10 μl of each sample were visualized by agarose gel electrophoresis and ethidium bromide staining and were positively identified by size, bcl-xγ fragments were further confirmed by Southern blot hybridization. The RT-PCR products amplified with bcl-xγ-specific primers were separated on agarose gels and blotted onto a nylon filter (Micron Separations Inc.) via upward capillary transfer in 20×SSC before filters were air-dried and subjected to UV-crosslinking.

Example 6

Expression of bcl-xγ

According to RT-PCR, bcl-xL (as well as bcl-xβ and bcl-xΔTM) is expressed in all tissues tested, including brain, eyes, heart, intestine, kidney, liver, lung, lymph nodes, and thymus (FIG. 3A), consistent with previous reports (L. H.

Figure 3:
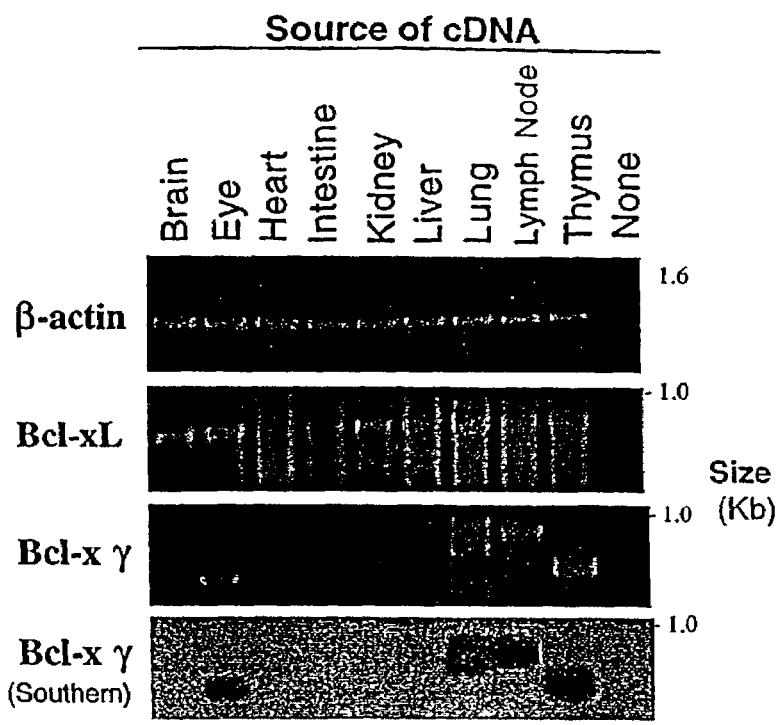
FIG. 3A shows expression of BCL-xy in different murine tissues by RT-PCR
FIG. 3B shows expression of BCL-x γ in lymph nodes of normal, nu/nu and Rag 2$^{-/-}$ mice.
FIG. 3C shows expression of BCL-x γ in the thymuses of normal, cortisone-treated and mutant mice as detected by RT-PCR.
Figure 3:
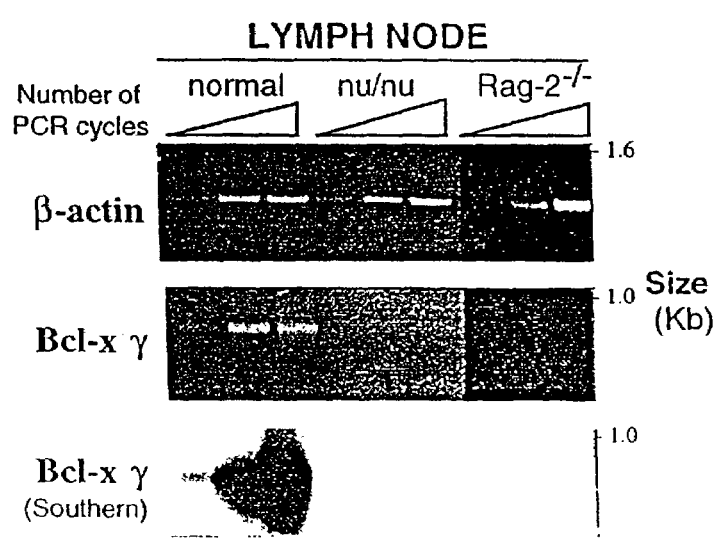

Boise et al., *Cell* 74, 597 (1993), M. Gonzalez-Garcia, et al., *Development* 120, 3033 (1994). Products were analyzed on 1% agarose gels stained with ethidium bromide. Molecular weight markers are indicated on the right margin of the gels. In contrast, bcl-xγ expression was detected in thymus, lymph node, lung and eye, but not brain, heart, intestine, kidney, liver (FIG. 3A). The specificity of the amplified bcl-xγ fragments in these tissues was confirmed by Southern blotting with a bcl-xγ-specific probe (FIG. 3A). The RT-PCR products amplified with bcl-xγ-specific primers were separated on agarose gels and blotted onto a nylon filter (Micron Separations Inc.) and subjected to UV-crosslinking. A 360 bp bcl-xγ-specific probe prepared by PCR amplification using the recombinant plasmid bclx7 encoding bcl-xγ as a template and using primers that do not overlap with the primers was used to detect gene expression followed by labeling with [α-$^{32}$P]dCTP (3000 Ci/mmol, NEN) by random oligomer priming (Oligolabeling kit, Pharmacia). The upstream (5'-GGTGTGAGTGGAGGTACA-3', SEQ ID NO:23) and downstream (5'-CCCCTCTGTTGATTTTCTG-3', SEQ ID NO:24) primers were used as probes. Radiolabeled probes were purified using Nick-spin columns (Pharmacia) to remove excess unincorporated radioactive nucleotides before used for hybridization overnight at 42° C. in 6×SSC buffer containing 50% formamide. The filters were washed in 2×SSC containing 0.1% SDS at 42° C. for 30 min. and in 0.2×SSC containing 0.1% SDS at 65° C. for 30 min. followed by autoradiography.

Failure to detect bcl-xγ in tissues such as brain, heart, intestine, kidney and liver by RT-PCR did not result from degraded preparations of RNA from these tissues since the ratio of ethidium bromide-stained 28S rRNA to 18S rRNA bands in agarose gels was the same for all tissues and bcl-xL, β-actin and other genes were successfully amplified by RT-PCR from the same RNA samples which were negative for bcl-xγ. These results indicate that expression of the bcl-xγ isoform is more restricted than other members of the bcl-x family.

Expression of bcl-xγ was tested in T-cells, B-cells or monocytes. bcl-xγ was not expressed in peripheral lymphoid tissues of Rag-2 deficient mice, consistent with its selective expression in lymphocytes. Furthermore, bcl-xγ was expressed in lymph nodes of BALB/c but not BALB/c nu/nu mice, suggesting that its expression is confined to T-lymphocytes (FIG. 3B). The analysis of cDNA from lymph nodes (LN) of normal, BALB/c nu/nu and Rag-2$^{-/-}$ mice indicated that bcl-x γ is amplified in LN of normal, but not nu/nu donors (PCR amplification of β-actin fragment served as control.

Additional analysis of bcl-xγ expression in the thymus indicated that it is not detectable in double negative (DN) cells from normal or recombinase-activating gene (RAG)-2 deficient (RAG-2$^{-/-}$) donors, nor in thymocytes from mice which are deficient in TCR-β chain and fail to undergo TCR-dependent maturation into double positive (DP) thymocytes. bcl-xγ is expressed by double positive (DP) thymocytes, since preparations that contained approximately 90% double positive (DP) and 10% single positive (SP) cells expressed bcl-xγ while purified SP thymocytes did not express detectable bcl-γ.

Figure 3C:
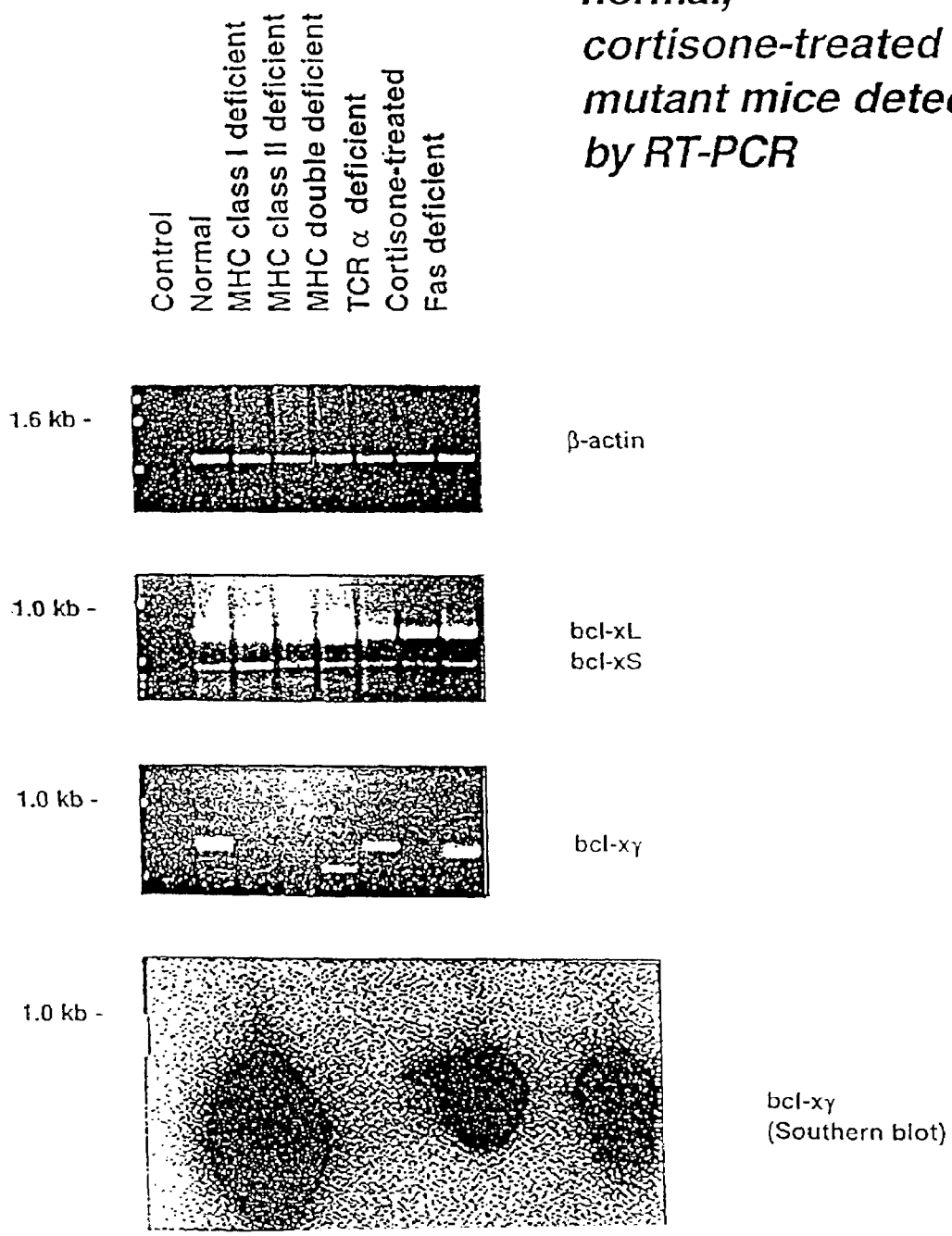

Bcl-xγ expression in DP thymocytes depends on engagement of the TCR by MHC/peptide ligands in the thymus, since bcl-xγ was not detectable in thymocytes from mutant mice deficient in MHC class I/II (MHC double-deficient mice) (FIG. 3C). By contrast, expression of bcl-xL and bcl-xS (and bcl-xβ, -ΔTM, not shown) was unchanged in thymocytes from both MHC double-deficient mice and TCR-β deficient mice, suggesting that expression of other bcl-x isoforms in the thymus does not depend on TCR ligation.

Expression of bcl-xγ in the thymuses of normal, cortisone-treated and mutant mice was also detected by RT-PCR. For cortisone treatment of mice, 2.5 mg/mouse of Cortisone Acetate (Merck Sharp and Dohme, U.S.A.) was injected i.p. into one-month old C57BL/6J mice 48 hours before animals were sacrificed as described previously [R. Scollay, K. Shortman, *Thymus* 5, 245 (1983)]. PCR analysis showed that expression of MHC class I and II, TCR-α, and Fas genes are not required for expression of bcl-xL and bcl-xS since in the thymuses from all of those mutant mice bcl-xL and bcl-xS were expressed in a comparable level. On the contrary, bcl-xγ was only expressed in the thymuses from normal mice, TCR-α knock-out mice and Fas gene mutant mice. The specificity of bcl-xγ fragments amplified in RT-PCR was confirmed by a Southern blot hybridization using a [32-P] dCTP-labeled bcl-xγ-specific probe which did not overlap with either primer used in RT-PCR. (FIG. 3C).

Example 7

Sequence Variations within the 3' Noncoding Region of bcl-xγ bcl-x γ is expressed differently in different murine tissues. The two observed sizes of bcl-x γ reflect nucleotide insertions within the 3' non-coding region according to cloning/DNA sequencing. The length and content of the 3' noncoding region may affect mRNA translational efficiency or stability (Tanguay and Gallic, 1996 *Mol. Cell. Biol.* 16, 146–156).

Example 8

Association of BCL-xγ with the T Cell Receptor

Figure 4A:
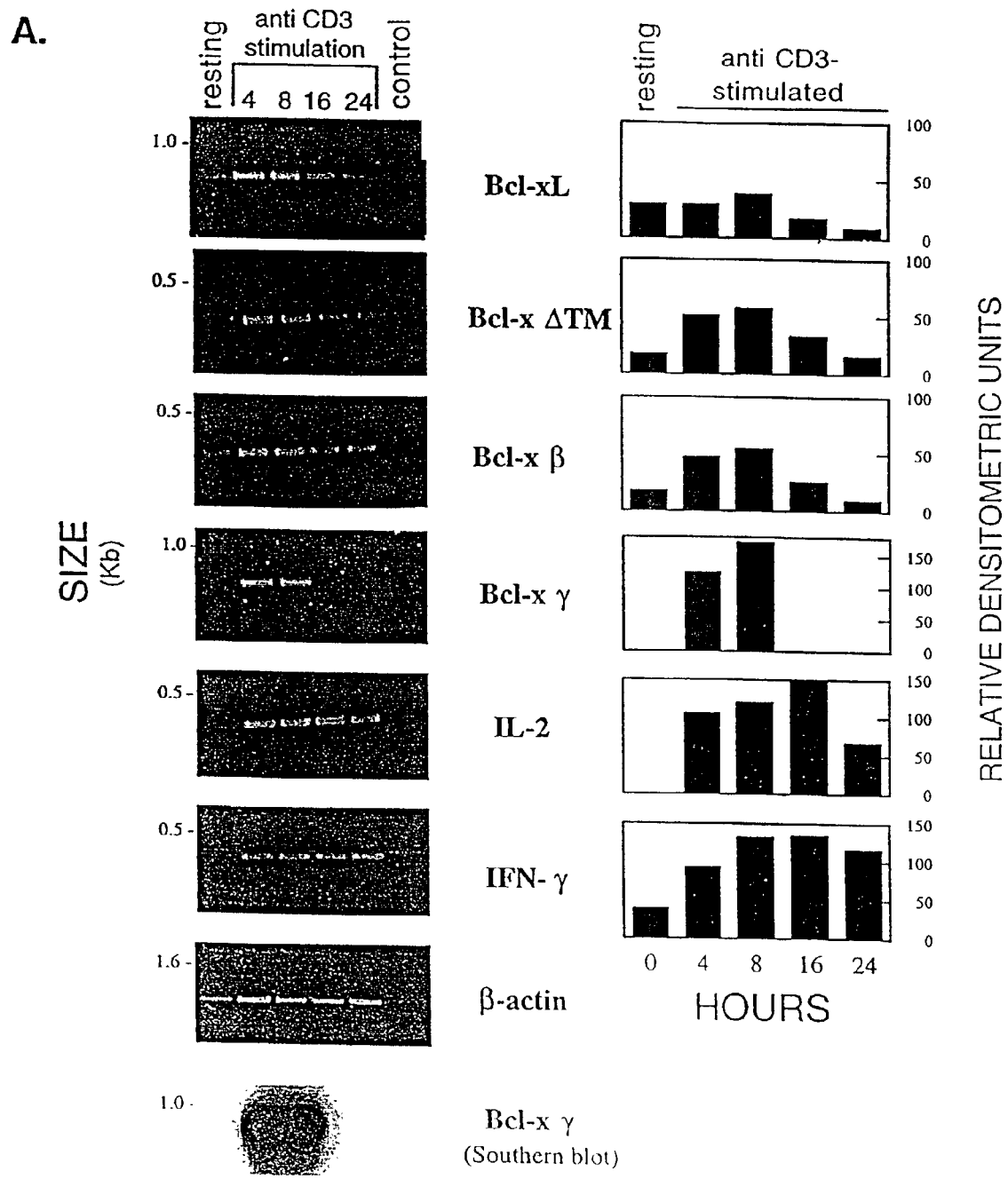
FIG. 4A shows expression of BCL-x isoforms in activated T-cells after CD3 ligation.
Figure 4B:
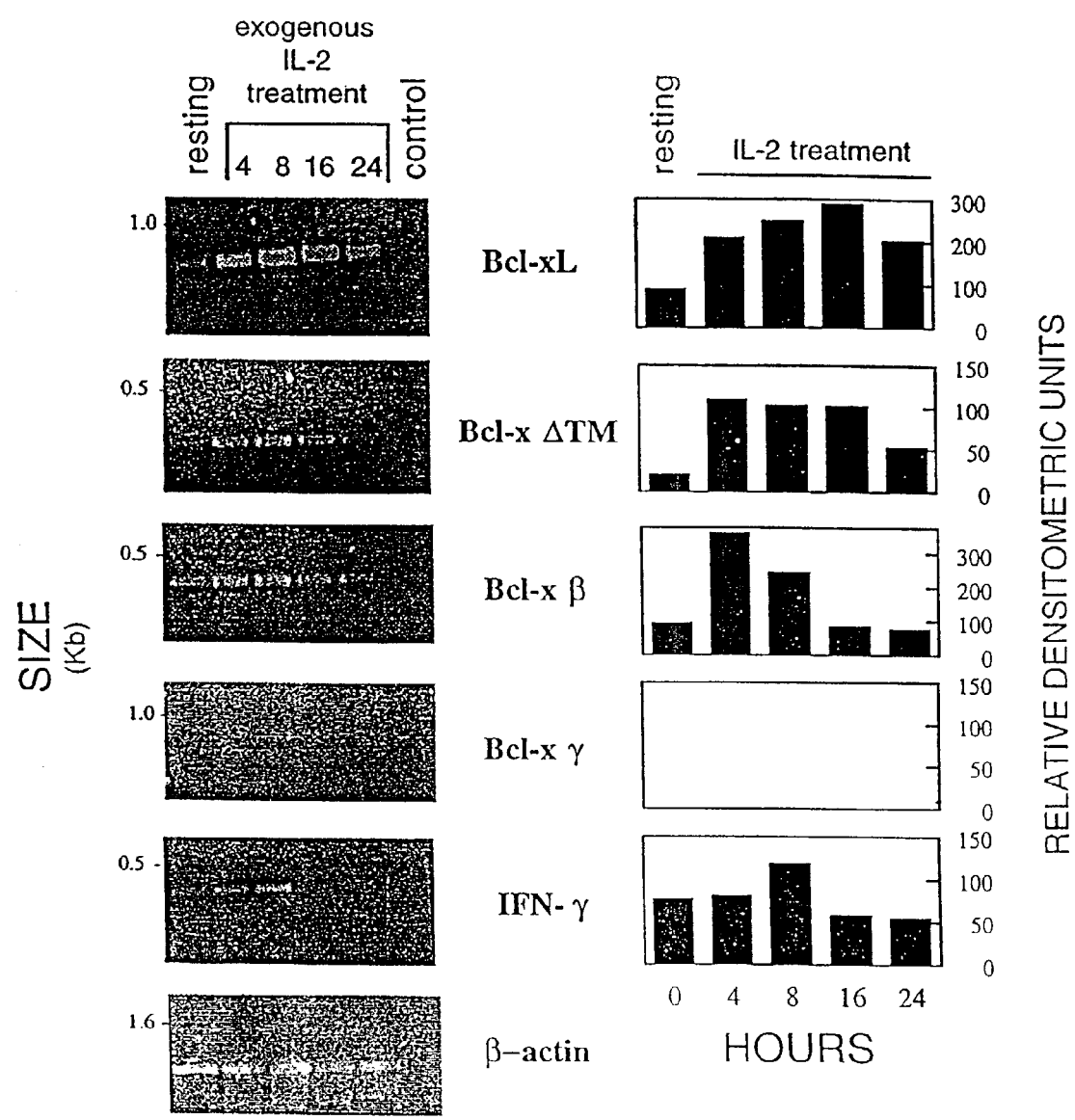
FIG. 4B shows expression of BCL-x isoforms in activated T-cells after interleukin-2 stimulation.

BCL-xγ expression was tested in a variety of cell types. O3 is a murine CD4+Th1 clone derived from BALB/c mice after in vitro selection for proliferation to OVA in association with presenting cells (APC) of BALB/c mice [S. Friedman, D. Sillcocks, H. Cantor, *Immuogenetics* 26, 193 (1987)]. The AF3.G7 hybridoma, generated by fusing cow insulin-immune C57BL/6 lymph node cells with the BW5147 thymoma line, expresses a $V_β6^+/V_α3.2^+$ TCR and responds to both cow insulin peptide and to MTV-7 according to IL-2 production [D. G. Spinella et al., *J. Immunol.* 138, 3991 (1987)]. EL4 is a mouse lymphoma cell line established in C57BL/6N mice which produces high titers of murine IL-2[J. Wein, E. Roberts, *Cancer Res.* 25, 1753 (1965)]. Bcl-xγ expression was not detectable in the resting murine $T_H1$ clone O3, but increased substantially by 4 hours after CD3 ligation (MM6). Bcl-xγ was not expressed after IL-2 activation of these cells, although T-cell [$^3$H]-TdR incorporation after IL-2 activation or CD3 ligation was similar (FIG. 4A,B). After exposure of O3 T-cells to plate-bound anti-CD3 antibody for the indicated intervals, total RNA was extracted and RT-PCR amplification by an interleukin-2 and interferon-γ fragment indicated activation as early as 4 hours. The specificity of BCL-xγ fragments amplified in RT-PCR was confirmed by a Southern blot hybridization using a [$^{32}$-P]dCTP-labeled BCL-xγ specific probe which did not overlap with either primer used in RT-PCR as described in FIG. 3A and was deliberately overexposed to detect weak hybridization in negative PCR lanes (negative groups). Primers specific for interleukin-2 and interferon-γ were used as positive controls for T cell activation in RT-PCR. Oligonucleotides used as primers for PCR amplification of the mouse interleukin-2 fragment were 5'-TTCAAGCTC-CACTTCAAGCTC-3' (SEQ ID NO:15) and 5'-GACA-GAAGGCTATCCATCTCC-3' (SEQ ID NO:16). Primer sequences for PCR amplification of the mouse interferon-γ fragment were 5'-TGCATCTTGGCTTTGCAGCTCTTC-CTCATG-3', SEQ ID NO:17 and 5'-TGGACCTGTGGGT-TGTTGACCTCAAACTTG-3', SEQ ID NO:18. PCR-amplified fragments were analyzed on agarose gels followed by scanning and quantitation using an IS-1000 digital imaging system (Alpha Innotech Corp.), adjusting for exposure times so that the intensity of DNA fragment signals corresponded to the linear range of densitometric detection. To ensure that comparisons of cDNA levels in different samples were based upon the same amount of cDNA in each sample, the area under the densitometric peak of each sample was divided by the area under the β-actin densitometric peak for the corresponding sample. The ratios of bcl-x isoforms and controls (IL-2, IFN-γ) cDNA to β-actin cDNA for each sample are shown in Relative Densitometric Units.

Bcl-xγ expression after IL-2 stimulation was not detectable even after the number of PCR cycles was increased to the maximal number (50 cycles) before polymerase activity becomes limiting (D. M. Coen, In: Current Protocols in Molecular Biology. Ed. Ausubel, et al. Greene Publishing Associates, Inc. and John Wiley & Sons, Inc., Volume 2, Chapter 15: 15.01 (1994). In contrast, all other murine Bcl-x isoforms (bcl-xL, -β, -ΔTM, -S) were expressed in resting O3 cells and displayed similar increments 8 hours after either IL-2R or CD3 ligation (FIGS. 4A,B). After incubation of O3 T-cells with 25 U/ml IL-2 resulting in levels of [$^3$H]-thymidine incorporation that were similar to that obtained after CD3 ligation, total RNA was extracted. These results show that BCL-xL, BCL-xβ and BCL-xΔTM are upregulated 4–24 hours after IL-2 treatment, but BCL-x γ expression is not detectable. The PCR amplified fragments on agarose gels were scanned, quantitated using the IS-1000 digital imaging system (Alpha Innotech Corp.) and normalized as described above. The results indicate that signaling through IL-2 receptor does not upregulate the expression of BCL-x γ. TCR-dependent expression of Bcl-xγ was not limited to non-transformed primary T-cell clones: neither the AF3.G7 insulin-specific T-cell hybridoma nor the EL4 lymphoma cell line expressed bcl-xγ unless CD3 was ligated, in contrast to all other bcl-x isoforms displayed constitutive expression in these cells which was not increased after TCR ligation.

Example 9

Effect on T Cell Apoptosis

Since studies of previously described BCL-x isoforms have indicated that they either enhance (L. H. Boise et al., Cell 74, 597 (1993), M. F. Clarke, et al., Proc. Natl. Acad. Sci. USA, 92 11024 (1995); A. J. Minn et al., J. Biol. Chem. 271, 6306 (1996) or inhibit (L. H. Boise et al., Cell 74, 597 (1993), M. Gonzalez-Garcia, et al., Development 120, 3033 (1994), W. Fang, J. J. Rivard, D. L. Mueller, T. W. Behrens, J. Immunol. 153, 4388 (1994), M. Gonzalez-Garcia, et al., Proc. Natl. Acad Sci. USA 92, 4304 (1995) apoptosis, the effect of stable Bcl-xγ expression on apoptosis following TCR ligation was tested. A stable cell line expressing BCL-x γ was constructed. The plasmid pRC/RSV containing enhancer-promoter sequences from the Rous sarcoma virus long terminal repeat (Invitrogen, San Diego Calif.) was used to construct pRC/RSV-Bcl-xL by inserting a 0.75 kb fragment which contained a full-length open reading frame of Bcl-xL. The pRC/RSV-bcl-xγ vector was constructed by inserting a 1.0 kb fragment containing the full-length ORF of bcl-xγ. Correct orientation of bcl-xL and bcl-xγ inserts in the recombinant vector was confirmed by restriction enzyme digestion and DNA sequencing. Stable expression of the CTLL-2 T cell line (a mouse T-cell line derived from C57BL/6 H. E. Broome, C. M. Dargan, S. Krajewski, J. C. Reed, 1995. J. Immunol. 155, 2311). was achieved after transfection in a 5×10$^6$/0.5 ml with 10 μg Xbal-linearized vector by electroporation in a Gene-Pulser II (BioRad, CA) at 270 Volts and 950 μF for 20 msec. Two days after transfection, T-cells were diluted into 96-well plates at 5×10$^3$/0.1 ml or 1×10$^4$/0.1 ml/well in media containing 750 μg/ml of G418 and after two weeks, individual clones resistant to G418 were selected, expanded and maintained in medium containing 250 μg/ml of G418. In addition, the empty vector pRC/RSV was used to simultaneously transfect and expand CTLL-2 cells according to the same protocol. RT-PCR was performed to confirm efficient expression of transfected bcl-x genes in the transfected clones using RNA and digested with RNAse-free DNAse before RT-PCR to avoid contamination in RNA preparations. cDNAs reversed transcribed from total RNAs from these transfectants and cells transfected with the pRC/RSV control vector was amplified with a vector specific primer paired with either a bcl-xL specific primer or a bcl-xγ specific primer, run on agarose gels and confirmed by Southern blot hybridization with a $^{32}$P-labeled DNA probe prepared from the cDNA coding for the Bcl-x common region.

Figure 5:
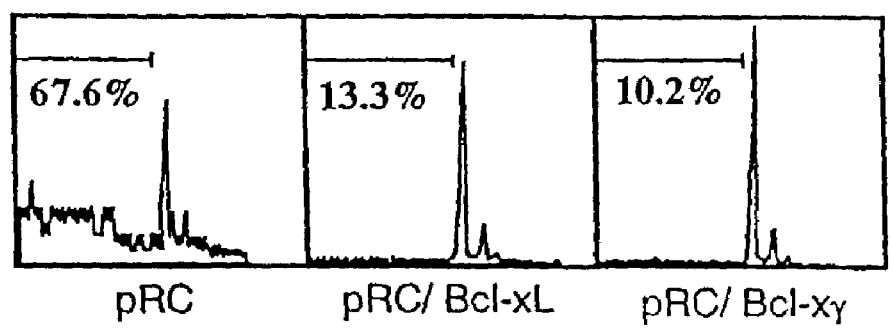
FIG. 5 shows apoptosis of BCL-x γ transfectants.

CD3 was ligated on CTLL-2 cells which stably overexpressed BCL-xγ (pRC/RSV-Bcl-xγ), BCL-xL (pRC/RSV-Bcl-xL) or a vector control (pRC/RSV). This led to apoptosis in 70% of the vector control transfectant cells, 10% of transfectants which overexpressed Bcl-xγ and 13% of transfectants which overexpressed Bcl-xL (FIG. 5). Plates precoated with anti-mouse CD3 antibody (Pharmingen, San Diego Calif.) (5 μml) were washed three times before addition of CTLL-2 clones that had been rinsed 3× with the IL-2-free RPMI 1640 medium supplemented with 5% FCS and incubated at 2 ml/well at a concentration of 1.25×10$^5$/ml at 37° C. for 24 hrs. Incubation medium was replaced with fresh RPMI 1640 medium supplemented with 5% FCS at 6 and 12 hours after plating cells to reduce secondary responses to potential growth factors secreted by cells activated after TCR ligation. The percentage of cells undergoing apoptosis for each transfected clones was analyzed by propidium iodide (PI) staining [A. J. McGahon et al., Meth. Cell Biol. 46, 153 (1995)]; H. E. Broome, C. M. Dargan, S. Krajewsky, J. C. Reed, J. Immunol. 155, 2311 (1995)]. Briefly, 24 hrs. after activation by plate-bound anti-CD3, cells were harvested, rinsed twice with cold PBS containing 5 mM EDTA, fixed with 50% ethanol in PBS containing 5 mM EDTA for 30 min at room temperature and treated with 40 μg/ml of DNAse-free RNAse A in PBS for 30 min and stained with 50 μg/ml of propidium iodide in PBS for 30 minutes before analysis in an Epics XL flow cytometry system using a standard setting of FL2 in semi-log mode (Coulter Inc.). Since partial loss of DNA from apoptotic cells due to activation of endogenous endonuclease(s) and/or marked condensation of the chromatin accompanies apoptosis and renders these areas of DNA inaccessible to PI staining, subdiploid cells with DNA concentrations lower than that of G0/G1 cells, were considered to be apoptotic [A. J. McGahon et al., Meth. Cell Biol. 46, 153 (1995)], while cells in G0/G1, S, G2/M phases were scored as viable. The cell cycle profile of CTLL-2 cells which stable express the indicated constructs after activation by plate-bound anti-CD3. The distribution of cells between the G1, S and G2/M phases of the cell cycle are shown; the abscissa indicates the relative cell number and the ordinate indicates DNA content based on PI staining of pRC vector-transfected cells, BCL-xL-transfected cells, and BCL-x γ-transfected cells. The numbers in the upper left corner represents the percent of cells which display apparent DNA contents of less than diploid (subdiploid), corresponding to the subpopulation of apoptotic cells. These stable trasfectants expressed similar levels of CD3 according to immunofluoresence and all had similar baseline levels of apoptosis (4–8%). These results are representative of three experiments.

Figure 6:
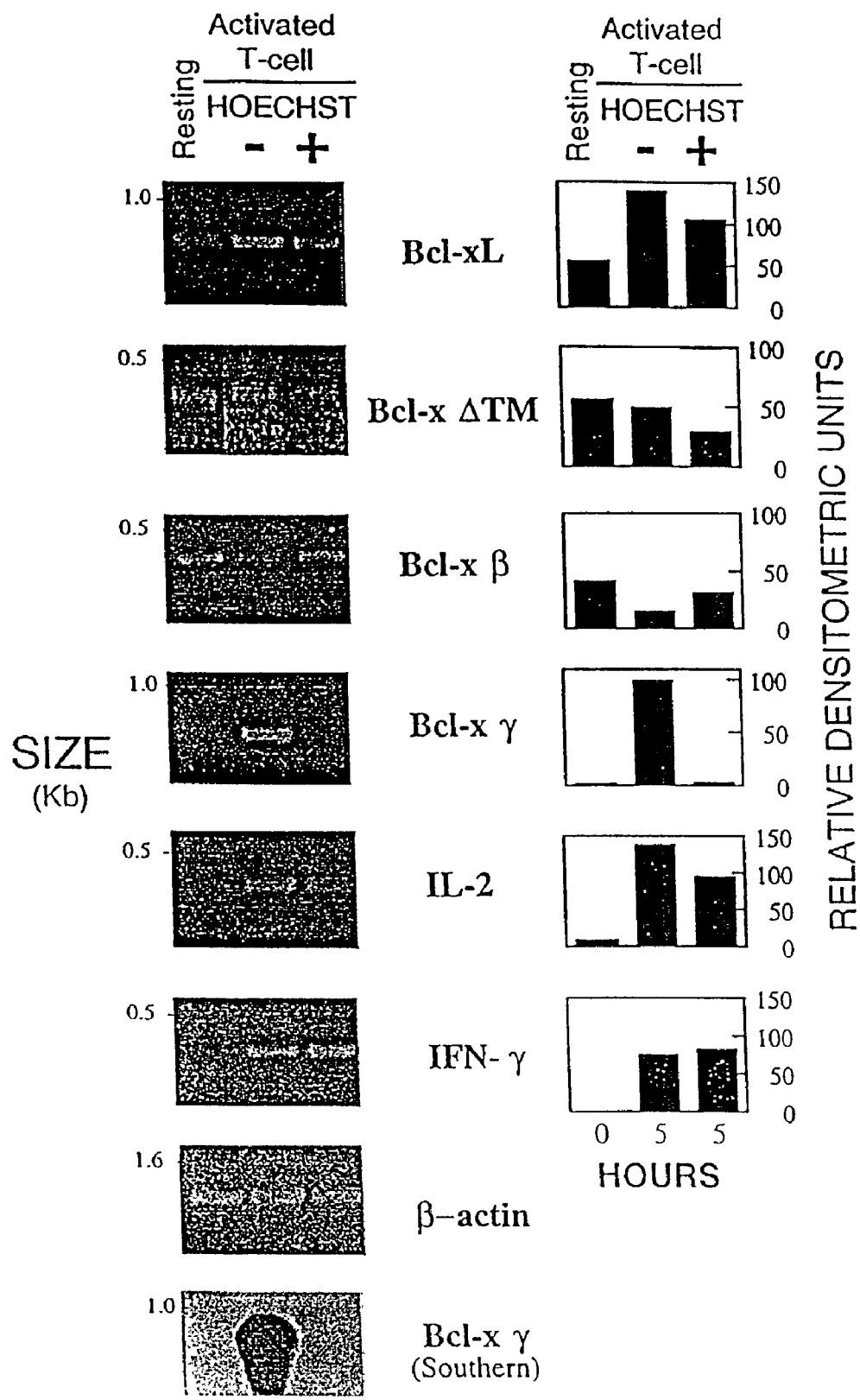
FIG. 6 shows expression of BCL-x isoforms in O3 T cell clone stimulated by plate-bound anti-CD3 antibody for 5 hours and sorted by flow cytometry.

These experiments, and previous transfection/overexpression studies, do not define the physiological role of endogenous Bcl-x expression in TCR -dependent apoptosis. Activated T-cells (including $T_H1$ clone O3) undergoing apoptosis after CD3 ligation stain intensely and specifically with Hoechst 33342 dye within 4–8 hours after activation, while the Hoechst-negative subpopulation of activated T-cells goes on to divide and produce cytokines (Weber et al. Immunity 2:363, 1995). O3 T cell clones ($1 \times 10^6$/ml) were cultured on plates pre-coated with anti-CD3-ε (5 μg/ml in PBS [$_p$H 8.5], Pharmingen; preincubated (37° C.) overnight) and incubated (37° C.) in DMEM plus 5% FBS before staining of activated O3 T cells with Hoechst 33342 dye and propidium iodide before analysis by flow cytometry, as described (M. G. Ormerod et al., *Cytometry* 14, 595 (1993). After gating out dead cells, activated T cell blasts were sorted into Hoechst-negative (non-apoptotic) and Hoechst-positive (apoptotic) subpopulations on a Becton-Dickinson FACS (G. F. Weber, S. Ambromson-Leeman, H. Contor, *Immunity* 2, 363 (1995). Activated O3 cells were analyzed for Bcl-x isoform expression after sorting into Hoechst-positive and Hoechst-negative fractions 5 hours after CD3 ligation. Bcl-xγ was strongly expressed in the successfully-activated Hoechst-negative fraction, but was not detectable in the Hoechst-positive fraction destined to undergo apoptosis (FIG. 6), even after maximum runs of 50 PCR cycles (D. M. Coen, In: *Current Protocols in Molecular Biology*. Ed. Ausubel, et al. Greene Publishing Associates, Inc. and John Wiley & Sons, Inc., Volume 2, Chapter 15: 15.01 (1994). In contrast, the BCL-xL, -xβ and -ΔTM isoforms were equally expressed in both the viable Hoechst-negative fraction and the apoptotic Hoechst-positive fraction of activated T-cells (FIG. 6). After stimulation of O3 T cell clone by plate-bound anti-CD3 antibody for 5 hours, the O3 cells were subjected to staining with Hoechst 33342 dye and propidium iodide. The results show that BCL-x γ is selectively expressed in Hoechst-negative cells but not in Hoechst-positive (apoptotic) cells while all other Bcl-x isoforms are expressed in both forms. Failure to detect BCL-x γ in Hoechst-positive cells did not result from degraded preparations of total RNA or cDNA, since β-actin and other BCL-x isoforms were detected in these samples. The PCR amplified fragments analyzed on agarose gel were scanned and quantitated using an IS-1000 digital imaging system (Alpha Innotech Corp.) followed by normalization, as described above. Failure of BCL-xγ expression after CD3 ligation represents a genetic marker of apoptosis, while activated T-cells that express BCL-xγ are spared. The tight coupling of BCL-xγ expression to the TCR may ensure that survival of activated T-cells is governed by the nature of TCR engagement rather than by non-specific cytokine stimuli. The observation that BCL-xγ, but not BCL-xL, expression by immature (DP) thymocytes requires host MHC products suggests that TCR ligation is also necessary for Bcl-xγ expression in this tissue. Possibly, expression of other isoforms such as BCL-xL may be important to guarantee survival of immature DP thymocytes long enough to provide a cellular substrate for positive and negative selection. Expression of BCL-xγ after TCR engagement may be necessary to allow successful positive selection, while failure to induce this gene product may result in cellular apoptosis and negative selection.

Example 10

BCL-xγ is Involved in Thymocyte Development

Figure 7:
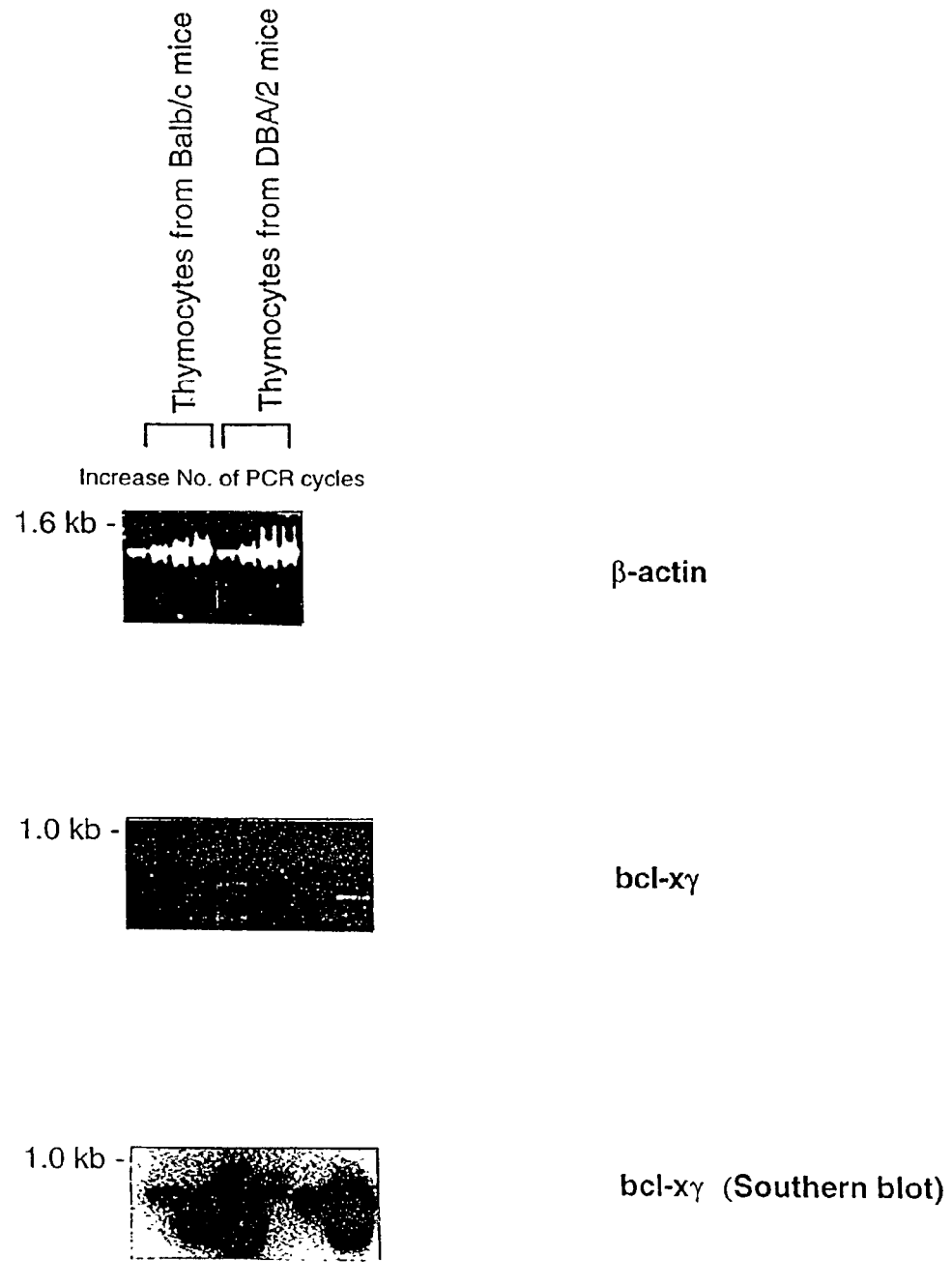
FIG. 7 shows expression of BCL-xγ in Balb/c thymocytes and DBA/2 thymocytes as detected by RT-PCR.

Thymocytes from Balb/c and DBA/2 mice were triple stained with flourescent antibodies against CD4, CD8, and Vb6. by flow cytometric cell sorting, $CD4^+CD8^{low}$ cells for the Vβ6+ subset were collected and analyzed for expression of β-actin and Bcl-x γ by RT-PCR (FIG. 7).

Figure 8:
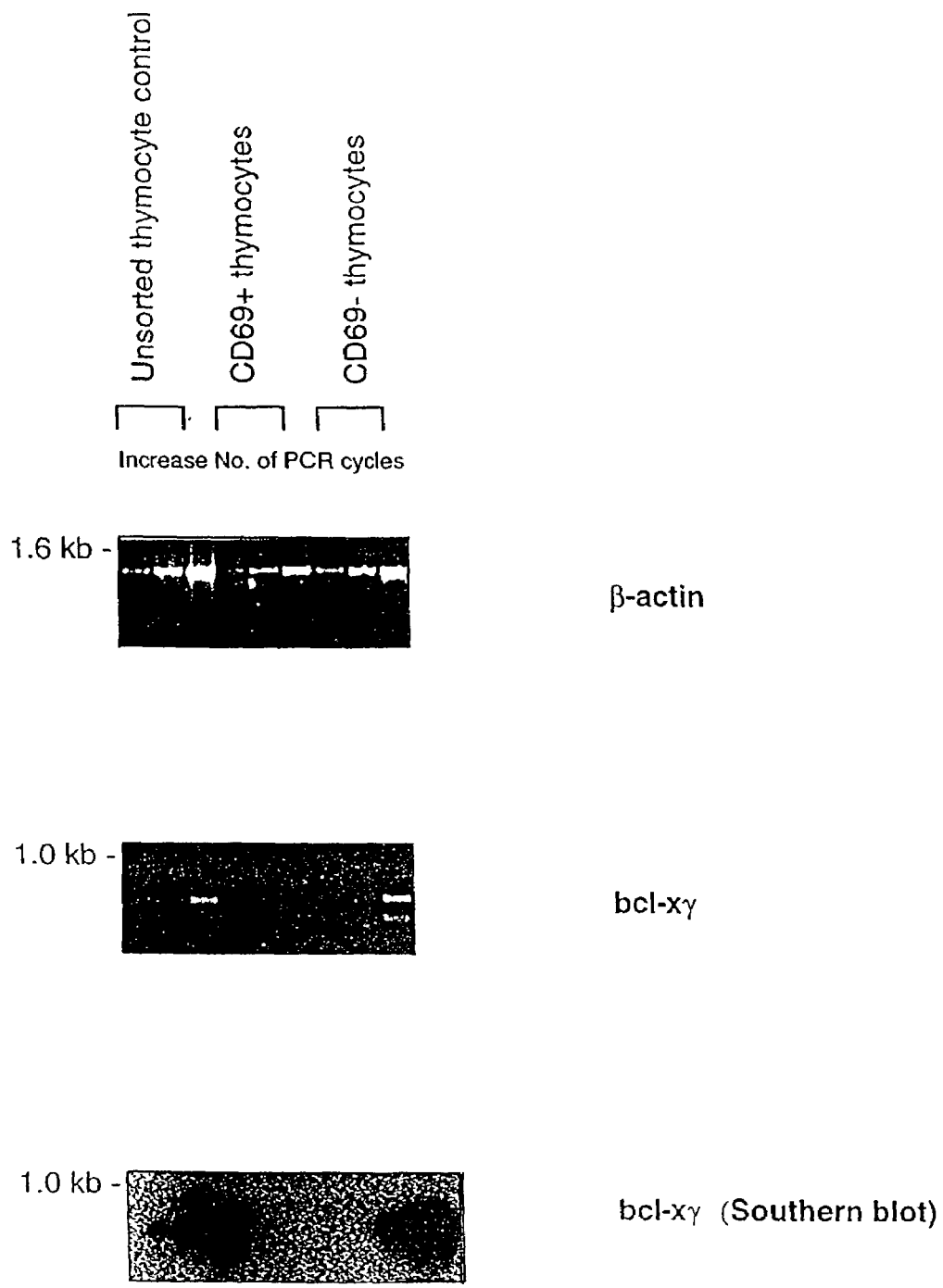
FIG. 8 shows expression of BCL-xγ in CD69+ and CD69− thymocytes as detected by RT-PCR

Thymocytes from C57B1/6 mice were labelled with biotinylated anti-CD69 antibody followed by precipitation with streptavidin-conjugated Dynabeads ($6 \times 10^8$ beads/ml, beads: target cells 10:1). Separation was confirmed by flow cytometry. Fractions were anayzed by RT-PCR for expression of β-actin and Bcl-x γ. BCL-xγ expression was confined to the CD69⁻ fraction of thymocytes (FIG. 8).

Figure 9:
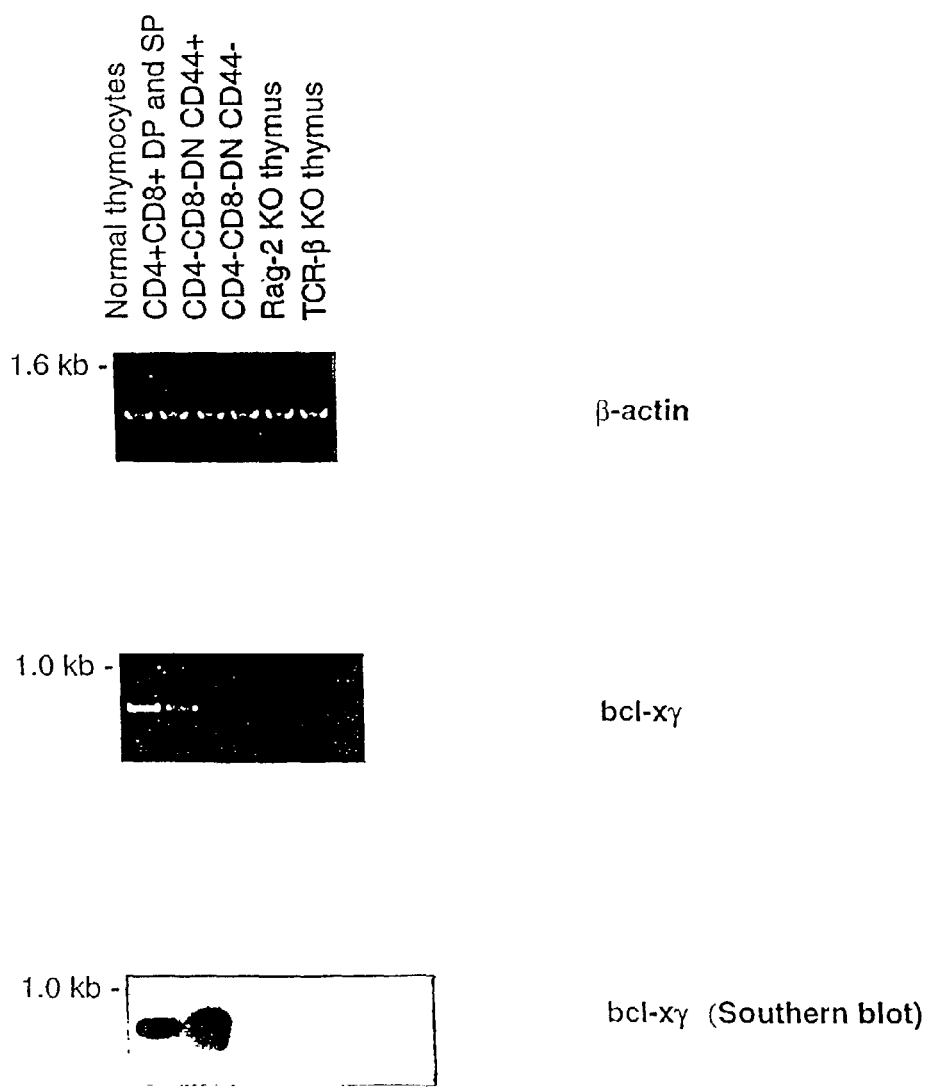
FIG. 9 shows expression of BCL-xy in thymocyte sub-populations.

Thymocytes from C57B1/6 mice were fractionated with anti-CD4 and anti-CD8 conjugated Dynabeads (beads:target cells 4:1). The supernatant fraction was separated into two subfractions by biotin anti-CD44 plus streptavidin-Dynabeads. Separation was confirmed by flow cytometry. Fractions were analyzed by RT-PCR for expression of β-actin and BCL-x γ (FIG. 9). Expression of BCL-x γ was not detected in double negative (DN) (CD4⁻ 8⁻) thymocytes (either CD44⁺ or CD44⁻) from normal, Rag-2⁻/⁻ or TCRβ⁻/⁻ donors, nor in single positive (SP) thymocytes (>95%).

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated protein, comprising an amino acid sequence at least 95% homologous to the amino acid sequence of SEQ ID NO: 2 and wherein said protein is anti-apoptotic.

2. An isolated protein, or a portion thereof, wherein the protein comprises amino acids 185–235 of SEQ ID NO: 2 and is anti-apoptotic.

3. An isolated protein, or portion thereof, comprising the amino acid sequence of SEQ ID NO: 2, wherein the protein or portion thereof is anti-apoptotic.

4. An isolated BCL-xγ fusion protein comprising the amino acid sequence of SEQ ID NO: 2 or a portion thereof, wherein the amino acid sequence of SEQ ID NO:2 or portion thereof is anti-apoptotic.

5. An isolated protein, or portion thereof, encoded by the nucleic acid sequence of SEQ ID NO: 1, wherein the protein or portion thereof is anti-apoptotic.

* * * * *

SEQUENCE LISTING

<160> NUMBER OF SEQ ID NOS: 26

<210> SEQ ID NO 1
<211> LENGTH: 1384
<212> TYPE: DNA
<213> ORGANISM: Mus musculus -continued

```
<220> FEATURE:
<221> NAME/KEY: CDS
<222> LOCATION: (378)..(1085)

<400> SEQUENCE: 1
cattcctcct gagataaggc cctcgatctg gtcgatggag gaaccaggtt gtgaggggggc      60 aggttcctaa gcttcgcaat tcctctgtcg ccttctgagc tgcctaccag gtcgcatgat     120
cctccggccg gggctggttt ttttttttt ttttttttt ttgctgagtt accggcgacc       180
cagccaccac ctcctccccg acctatgata caaaagacct tccgggggtt gtacctgctt     240
gctgtcgccg gagatagatt tgaataacct tatcttggct ttggatcctg aagagaatc      300 gctaaacaca gagcagaccc agtaagtgag caggtgtttt ggacaatgga ctggttgagc     360
```

| | | | | | | | | | | | |
|---|---|---|---|---|---|---|---|---|---|---|---|
| ccatctctat tataaaa atg tct cag agc aac cgg gag ctg gtg gtc gac | | | | | | | | | | | 410 |
| | Met Ser Gln Ser Asn Arg Glu Leu Val Val Asp | | | | | | | | | | |
| | 1 | | | 5 | | | | | 10 | | |

| ttt ctc tcc tac aag ctt tcc cag aaa gga tac agc tgg agt cag ttt | 458 |
|---|---|
| Phe Leu Ser Tyr Lys Leu Ser Gln Lys Gly Tyr Ser Trp Ser Gln Phe | |
| 15   20   25 | |

| agt gat gtt gaa gag aat agg act gag gcc cca gaa gaa act gaa gca | 506 |
|---|---|
| Ser Asp Val Glu Glu Asn Arg Thr Glu Ala Pro Glu Glu Thr Glu Ala | |
| 30   35   40 | |

| gag agg gag acc ccc agt gcc atc aat ggc aac cca tcc tgg cac ctg | 554 |
|---|---|
| Glu Arg Glu Thr Pro Ser Ala Ile Asn Gly Asn Pro Ser Trp His Leu | |
| 45   50   55 | |

| gcg gat agc ccg gcc gtg aat gga gcc act ggc cac agc agc agt ttg | 602 |
|---|---|
| Ala Asp Ser Pro Ala Val Asn Gly Ala Thr Gly His Ser Ser Ser Leu | |
| 60   65   70   75 | |

| gat gcg cgg gag gtg att ccc atg gca gca gtg aag caa gcg ctg aga | 650 |
|---|---|
| Asp Ala Arg Glu Val Ile Pro Met Ala Ala Val Lys Gln Ala Leu Arg | |
| 80   85   90 | |

| gag gca ggc gat gag ttt gaa ctg cgg tac cgg aga gcg ttc agt gat | 698 |
|---|---|
| Glu Ala Gly Asp Glu Phe Glu Leu Arg Tyr Arg Arg Ala Phe Ser Asp | |
| 95   100   105 | |

| cta aca tcc cag ctt cac ata acc cca ggg acc gcg tat cag agc ttt | 746 |
|---|---|
| Leu Thr Ser Gln Leu His Ile Thr Pro Gly Thr Ala Tyr Gln Ser Phe | |
| 110   115   120 | |

| gag cag gta gtg aat gaa ctc ttt cgg gat gga gta aac tgg ggt cgc | 794 |
|---|---|
| Glu Gln Val Val Asn Glu Leu Phe Arg Asp Gly Val Asn Trp Gly Arg | |
| 125   130   135 | |

| atc gtg gcc ttt ttc tcc ttt ggc ggg gca ctg tgc gtg gaa agc gta | 842 |
|---|---|
| Ile Val Ala Phe Phe Ser Phe Gly Gly Ala Leu Cys Val Glu Ser Val | |
| 140   145   150   155 | |

| gac aag gag atg cag gta ttg gtg agt cgg att gca agt tgg atg gcc | 890 |
|---|---|
| Asp Lys Glu Met Gln Val Leu Val Ser Arg Ile Ala Ser Trp Met Ala | |
| 160   165   170 | |

| acc tat ctg aat gac cac cta gag cct tgg atc cag gag aac ggc ggc | 938 |
|---|---|
| Thr Tyr Leu Asn Asp His Leu Glu Pro Trp Ile Gln Glu Asn Gly Gly | |
| 175   180   185 | |

| tgg ggt gtg agt gga ggt aca ccc ctc aga tct gtc ttc aga agg ctt | 986 |
|---|---|
| Trp Gly Val Ser Gly Gly Thr Pro Leu Arg Ser Val Phe Arg Arg Leu | |
| 190   195   200 | |

| gtt caa gtg cca gga gtg gcg gag cac gtt tgt gat ccc agc ctt tgg | 1034 |
|---|---|
| Val Gln Val Pro Gly Val Ala Glu His Val Cys Asp Pro Ser Leu Trp | |
| 205   210   215 | |

| gag gtg gaa aca gaa gga tcg gaa gtt caa ggc cct cct cag cta tta | 1082 |
|---|---|
| Glu Val Glu Thr Glu Gly Ser Glu Val Gln Gly Pro Pro Gln Leu Leu | |
| 220   225   230   235 | |

```
tag gtttctctgt gtagccctgg ctgtcctgta actcactctg tagagcaaac            1135
```

```
tggactcaaa ctcagagaca tgcctgcctg atcttcatcg tgagtgctgg aatcacaggc    1195
tctaacatgg ctatcgggag atgcgtggac caggcctatg gtggcccttg acgcagcgtg    1255
gtgcttcaac tcagaccaag agacagagca gaaaatcaac agaggggaca aaaagtgtct    1315
gtgtgccaag gaccttatct caggaggact tcaggaagga cgctgaccct tccttccctc    1375
attccttcg                                                            1384

<210> SEQ ID NO 2
<211> LENGTH: 235
<212> TYPE: PRT
<213> ORGANISM: Mus musculus

<400> SEQUENCE: 2

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Glu Thr Glu Ala Glu Arg Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ser Trp Met Ala Thr Tyr Leu Asn Asp
                165                 170                 175

His Leu Glu Pro Trp Ile Gln Glu Asn Gly Gly Trp Gly Val Ser Gly
            180                 185                 190

Gly Thr Pro Leu Arg Ser Val Phe Arg Arg Leu Val Gln Val Pro Gly
        195                 200                 205

Val Ala Glu His Val Cys Asp Pro Ser Leu Trp Glu Val Glu Thr Glu
    210                 215                 220

Gly Ser Glu Val Gln Gly Pro Pro Gln Leu Leu
225                 230                 235

<210> SEQ ID NO 3
<211> LENGTH: 102
<212> TYPE: DNA
<213> ORGANISM: Mus musculus

<400> SEQUENCE: 3
gctcccactg atctctccag gattgcctat caatgccaga gaccagctag cactctgctg    60
cctctcagat gcaagagcac acccacgctc agaagactga gg                      102

<210> SEQ ID NO 4
<211> LENGTH: 79
```

```
<212> TYPE: DNA
<213> ORGANISM: Mus musculus

<400> SEQUENCE: 4
aagaaaggtc tcctctgtga agccaaggac ttggtcatat atactgcagc atcccccgag        60
cctgggatct tactattag                                                    79

<210> SEQ ID NO 5
<211> LENGTH: 60
<212> TYPE: DNA
<213> ORGANISM: Homo sapiens

<400> SEQUENCE: 5
ggggtgatgt ggagctggga tgtcaggtca ctgaatgccc gccggtaccg cagttcaaac        60

<210> SEQ ID NO 6
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 6
tcgctcgccc acatcccagc ttcacataac ccc                                    33

<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 7
ctggttcggc ccacgtcctt cctgaagtcc tcc                                    33

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 8
ccgggaattc atctcagagc aaccgggagc tggtg                                  35

<210> SEQ ID NO 9
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 9
ccaggaattc ggatcccgtc cttcctgaag tcctcct                                37

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10
ccaccaacaa gacaggct                                                     18
```

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
ctctcctccc tcacacaccc ctctc                                    25

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
aagatacagg tcccttaaa                                           19

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
atggatgacg atatcgctgc                                          20

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
ctagaagcac ttgcggtgca c                                        21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
ttcaagctcc acttcaagct c                                        21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
gacagaaggc tatccatctc c                                        21

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 17
tgcatcttgg ctttgcagct cttcctcatg                                30

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 18
tggacctgtg ggttgttgac ctcaaacttg                                30

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
tctacagagt gagttacag                                            19

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
cccctctgtt gattttctg                                            19

<210> SEQ ID NO 21
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 21
ccgggaattc ggatcccgtc cttcctgaag tcctcct                        37

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
gggtgtacct ccactcacac c                                         21

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
ggtgtgagtg gaggtaca                                             18

<210> SEQ ID NO 24

```
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 24
cccctctgtt gattttctg                                               19

<210> SEQ ID NO 25
<211> LENGTH: 14
<212> TYPE: PRT
<213> ORGANISM: Artificial Sequence
<220> FEATURE:
<223> OTHER INFORMATION: Illustrative consensus sequence
<220> FEATURE:
<221> NAME/KEY: MOD_RES
<222> LOCATION: (2)..(7)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Xaa can be any naturally occurring amino acid
<220> FEATURE:
<221> NAME/KEY: MOD_RES
<222> LOCATION: (13)..(14)
<223> OTHER INFORMATION: Xaa can be any naturally occurring amino acid

<400> SEQUENCE: 25

Asn Xaa Xaa Xaa Xaa Xaa Xaa Gly Xaa Thr Pro Leu Xaa Xaa
 1               5                  10

<210> SEQ ID NO 26
<211> LENGTH: 33
<212> TYPE: PRT
<213> ORGANISM: Artificial Sequence
<220> FEATURE:
<223> OTHER INFORMATION: Illustrative consensus sequence
<220> FEATURE:
<221> NAME/KEY: MOD_RES
<222> LOCATION: (2)..(7)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Xaa can be any naturally occurring amino acid
<220> FEATURE:
<221> NAME/KEY: MOD_RES
<222> LOCATION: (14)..(14)
<223> OTHER INFORMATION: Xaa can be any naturally occurring amino acid
<220> FEATURE:
<221> NAME/KEY: MOD_RES
<222> LOCATION: (16)..(24)
<223> OTHER INFORMATION: Xaa can be any naturally occurring amino acid
<220> FEATURE:
<221> NAME/KEY: MOD_RES
<222> LOCATION: (26)..(27)
<223> OTHER INFORMATION: Xaa can be any naturally occurring amino acid
<220> FEATURE:
<221> NAME/KEY: MOD_RES
<222> LOCATION: (30)..(31)
<223> OTHER INFORMATION: Xaa can be any naturally occurring amino acid

<400> SEQUENCE: 26

Asn Xaa Xaa Xaa Xaa Xaa Xaa Gly Xaa Thr Pro Leu His Xaa Ala Xaa
 1               5                  10                  15

Xaa Xaa Xaa Xaa Xaa Xaa Xaa Xaa Val Xaa Xaa Leu Leu Xaa Xaa Gly
                20                  25                  30

Ala
```